(12) United States Patent
Niemiec et al.

(10) Patent No.: US 12,357,721 B1
(45) Date of Patent: Jul. 15, 2025

(54) COMBINATION MOBILE BUILT-IN AIR FLOW MECHANISM AND LED KILL CHAMBER

(71) Applicants: Darrin W. Niemiec, Schaumburg, IL (US); William J. Carlson, Schaumburg, IL (US)

(72) Inventors: Darrin W. Niemiec, Schaumburg, IL (US); William J. Carlson, Schaumburg, IL (US)

(73) Assignee: Go Fan Yourself, LLC, Long Grove, IL (US)

(*) Notice: Subject to any disclaimer, the term of this patent is extended or adjusted under 35 U.S.C. 154(b) by 0 days.

(21) Appl. No.: 18/675,455

(22) Filed: May 28, 2024

Related U.S. Application Data

(63) Continuation of application No. 18/122,321, filed on Mar. 16, 2023, now Pat. No. 11,993,677, which is a continuation of application No. 17/739,337, filed on May 9, 2022, now Pat. No. 11,608,411, which is a continuation-in-part of application No. 16/943,352,
(Continued)

(51) Int. Cl.
| | |
|---|---|
| A61L 9/20 | (2006.01) |
| F21L 2/00 | (2006.01) |
| F21S 8/04 | (2006.01) |
| F21Y 113/00 | (2016.01) |
| F21Y 115/10 | (2016.01) |

(52) U.S. Cl.
CPC ............. *A61L 9/20* (2013.01); *A61L 2209/11* (2013.01); *A61L 2209/12* (2013.01); *A61L 2209/15* (2013.01); *F21L 2/00* (2013.01); *F21S 8/04* (2013.01); *F21Y 2113/30* (2023.05); *F21Y 2115/10* (2016.08)

(58) Field of Classification Search
CPC ............. A61L 9/20; A61L 2209/11–12; A61L 2209/15; F21L 2/00; F21S 8/04; F21Y 2113/30; F21Y 2115/10
See application file for complete search history.

(56) References Cited

U.S. PATENT DOCUMENTS

| | | |
|---|---|---|
| 7,922,351 B2 | 4/2011 | Welker |
| 8,350,228 B2 | 1/2013 | Welker |
| (Continued) | | |

FOREIGN PATENT DOCUMENTS

| | | |
|---|---|---|
| CN | 107496969 A | 12/2017 |

OTHER PUBLICATIONS

Information Disclosure Statement filed in U.S. Appl. No. 18/045,707, Oct. 11, 2022.
(Continued)

*Primary Examiner* — James R Greece
*Assistant Examiner* — Jose M Diaz
(74) *Attorney, Agent, or Firm* — Vitale, Vickrey, Niro, Solon & Gasey, LLP

(57) ABSTRACT

Disclosed embodiments relate to a combination axial fan and LED lighting system configured to fit into the footprint of a standard ceiling tile. Disclosed embodiments further include ceiling tiles with a built-in fan and/or LED lighting. The disclosed systems may include one or more UV-C light sources which irradiate contaminants as air flows through the UV-C unit. The UV-C unit is mounted on either a universal mounting mechanism or a mobile support unit to provide mobility to the UV-C unit.

20 Claims, 26 Drawing Sheets

Related U.S. Application Data filed on Jul. 30, 2020, now Pat. No. 11,332,573, which is a continuation-in-part of application No. 16/377,750, filed on Apr. 8, 2019, now Pat. No. 11,028,223, which is a continuation of application No. 16/157,874, filed on Oct. 11, 2018, now Pat. No. 10,316,141, which is a continuation-in-part of application No. 16/040,189, filed on Jul. 19, 2018, now Pat. No. 10,221,857, which is a continuation-in-part of application No. 15/589,367, filed on May 8, 2017, now Pat. No. 10,247,191, which is a continuation-in-part of application No. 15/471,762, filed on Mar. 28, 2017, now Pat. No. 10,006,619.

(60) Provisional application No. 62/439,719, filed on Dec. 28, 2016.

(56) References Cited

U.S. PATENT DOCUMENTS

| | | | |
|---|---|---|---|
| 8,439,517 | B2 | 5/2013 | Welker |
| 9,737,842 | B2 | 8/2017 | Matlin |
| 11,608,411 | B2 * | 3/2023 | Niemiec .................. F24F 8/80 |
| 2015/0250913 | A1 | 9/2015 | Matsui |
| 2023/0061420 | A1 | 3/2023 | Higgins |
| 2023/0119976 | A1 | 4/2023 | Maletich |
| 2023/0366570 | A1 | 11/2023 | Maletich |
| 2024/0157016 | A1 | 5/2024 | Losser |

OTHER PUBLICATIONS https://web.archive.org/web/20160717150658/http://vidashield.com/files/VidaShield-Trifold.pdf (brochure captured by WBM).
https://web.archive.org/web/20160804101125/http://vidashield.com/files/VS03.pdf (spec sheet captured by WBM), dated Jun. 25, 2016.

* cited by examiner

COMBINATION MOBILE BUILT-IN AIR FLOW MECHANISM AND LED KILL CHAMBER

This application is a continuation-in-part of application Ser. No. 16/943,352, filed on Jul. 30, 2020, which is a continuation-in-part of application Ser. No. 16/377,750, filed on Apr. 8, 2019, issued as U.S. Pat. No. 11,028,223 on Jun. 8, 2021, which is a continuation of application Ser. No. 16/157,874 filed on Oct. 11, 2018 issued as U.S. Pat. No. 10,316,141 on Jun. 11, 2019, which is a continuation-in-part of application Ser. No. 16/040,189, filed on Jul. 19, 2018, issued as U.S. Pat. No. 10,221,857 on Mar. 5, 2019, which is a continuation-in-part of application Ser. No. 15/589,367, filed on May 8, 2017, issued as U.S. Pat. No. 10,247,191 on Apr. 2, 2019, which is a continuation-in-part of application Ser. No. 15/471,762, filed on Mar. 28, 2017, issued as U.S. Pat. No. 10,006,619 on Jun. 26, 2018, which claims priority from Provisional Patent Application Ser. No. 62/439,719 filed Dec. 28, 2016.

FIELD OF THE INVENTION

The present inventions relate to an apparatus having a mobile built-in air flow mechanism and optional LED lighting for maintaining proper air quality and air movement in an indoor environment. Embodiments of the inventions further include a UV light source which decontaminates air as it flows through the apparatus and thus helps prevent the spread of bacteria, fungus, viruses and/or mold, etc. The apparatus may be adapted to be accommodated within a ceiling tile, a light fixture or other structure. The apparatus may also be mounted on a mobile support structure.

BACKGROUND OF THE INVENTION

Indoor spaces such as offices, hospitals, retail stores, educational institutions and the like have two main issues: (1) maintaining proper air quality and air movement; and (2) providing adequate lighting. Indoor spaces often have only a single HVAC system that provides air and heat to all of the different sized offices or rooms within a space. Separately, the indoor space utilizes a series of LED lights that may be mounted in ceiling tiles having a dimension of 2 ft.×2 ft. or 2 ft.×4 ft. Additionally, the ceiling may include canned, recessed lighting or a dropped-lighting fixtures. The present invention could be incorporated into those fixtures as well. Finally, it is understood that the present invention could be installed in any structure within a building, and could also be incorporated into a portable unit. The ceiling tile design is very similar to the design used in wall units or floor units. The configuration of the unit does not necessarily change if it is placed in a wall unit, floor unit or ceiling tile. The nature of the present invention is not affected by the placement of the apparatus.

There is a need for a system which can move air within an indoor space which supplements the primary HVAC system while at the same time providing ample lighting within the indoor space while fitting into the dimensions of a ceiling tile. The system also can provide a cooling effect on the LED lights to prolong the life-span of the lights.

According to the U.S. Department of Energy (DOE), more than 360 million troffers provide general lighting in commercial building interiors. With their standard dimensions of 2 ft.×4 ft., 1 ft.×4 ft. and 2 ft.×2 ft., these luminaires are popular in dropped, acoustical-tile ceilings with a low ceiling height (less than or equal to 9 feet). The installed troffer base is predominantly linear fluorescent. In recent years, the development of LED technology has resulted in a broad selection of products designed to challenge fluorescent, offering up to 70 percent energy savings, longer life and controllability.

There does exist a problem with LED lights. Excessive heat causes damage to LED lights. LED bulbs that produce white light typically generate excessive heat that must be conducted away from the LED light system. Proper thermal management is critical to maintaining the original brightness and extending the lifespan of LED lights. Unfortunately, due to component costs, many manufacturers do not include the materials or structures necessary to provide proper heat transfer, thereby reducing the performance of the product. For example, most LED lighting manufacturers use less expensive and less reliable circuit boards that do not transfer heat well. Heat build-up in LED lights will damage the material, decrease the effectiveness of the light and decrease the lifespan of the lighting unit.

The secret to extending the useful life of an LED fixture is proper thermal management. There are several factors that affect the thermal performance of any fixture including the ambient air temperature, but LEDs specifically suffer from improper thermal design. The displacement of waste heat produced by LED lights is paramount to the longevity of the LED lights and can provide an advantage to a company in the emerging LED lighting industry.

The energy consumed by an incandescent bulb produces around 12% heat, 83% infrared radiation and only 5% visible light. A typical LED light produces 15% visible light and 85% heat. It is important to dissipate heat from LED's through efficient thermal management. The operating temperature of an LED light affects the lifespan of the LED. LED lights do not tend to fail catastrophically, instead the lumen output of the LED decreases over time. Elevated internal temperatures of the LED cause accelerated deterioration of the LED lights.

One of the major complaints levied by people working in an office, school, hospital, or commercial space concerns the temperature in the space. Complaints about temperatures are not just a matter of employees' preferences and tolerances. Temperature has been found to have a direct correlation to productivity. It is believed that productivity is linked to the temperature of the building. In addition to temperature issues within a building, employees may experience headaches, dizziness, nausea, irritation, cough, fatigue, asthma and other symptoms due to what has been termed "sick building syndrome." The primary sources of indoor air quality problems are believed to be inadequate ventilation and contamination from within the building.

Further, in an office, hospital or other indoor environment, the absence of adequate ventilation causes irritating or harmful contaminants to accumulate, which causes worker discomfort, health problems and reduced performance levels. Such harmful contaminants include bacteria, fungus, mold or viruses that can cause people to become sick. There is a need for an air circulation mechanism which reduces airborne contaminants. Air purification is an important part of an HVAC system. A typical indoor HVAC system is not a substitute for source control or ventilation.

The inventions address the need for circulating air within a closed environment such as a school room, a hospital room or an office. The invention provides for a circulating air within that space through a separate virus or bacteria kill chamber. There is also a need to create what is called a virus or bacteria kill chamber. The kill chamber, or kill zone, must be self-enclosed such that any UV light source does not exit the kill chamber. The present invention operates to function as a separate and supplemental air circulation apparatus separate and apart from the HVAC system that provides the heating and cooling for the specific space.

Moreover, it would be advantageous for an air circulation mechanism to fit within the footprint of a typical ceiling tile. Likewise, there is a need for the air circulation device to be mounted on a mobile structure such that the air circulation device may be positioned at different locations within a room.

SUMMARY OF THE INVENTION

The present inventions relate to a ceiling tile with a built-in fan for circulating air. Embodiments of the inventions may further include one or more LED strips for lighting the environment in which the ceiling tiles are installed. Further yet, embodiments of the inventions may include one or more UV lights which irradiate the air flow, thereby removing airborne contaminants such as viruses, superbugs, mold, etc.

In some embodiments of the inventions, an air circulation device may comprise: a ceiling tile; at least a first fan mounted to the ceiling tile; a first vent in the ceiling tile; and a baffle, mounted to the ceiling tile, and defining at least a first airway between the fan and the first vent. A first LED strip may be mounted to the ceiling tile. Further embodiments may comprise at least a second vent, and a second LED strip and form a second airway between the fan and the second vent. The air circulation may further comprise at least a second fan, wherein the first and second fans are configured in-line to direct air into the first and second airway. In some embodiments, the first and second fans are configured as air in-takes and air is exhausted through the first and second vents, and the first and second fans are configured to rotate in opposite directions.

Further yet, embodiments may include an air diversion mechanism configured to divert air from the first and second fan to the first and second airway. A first UV light source may be mounted in the first airway. In some embodiments, a second UV light source is mounted in the second airway. In other embodiments, the first and second airways are lined with a UV-reflective material. Moreover, the UV-reflective material may be stainless steel. The first and second UV light sources may emit UV-C light waves having a wavelength between 200 to 280 nanometers. The first and second UV light sources may be configured to be activated and deactivate via a remote control. The ceiling tile may be a drywall structure. In other embodiments, the ceiling tile is an acoustic panel.

The inventions include an air purifying device, comprising: an apparatus having at least one vent; a fan mounted to a housing within the apparatus; a baffle defining at least a first airway between the fan and the vent; and at least a first UV light source mounted in the first airway, wherein the first airway accommodates a UV-reflective material in at least a portion of the first airway; and wherein a first UV-screen is attached to the first airway to block UV light from exiting the airway. The inventors understood that the air purifying apparatus of the present invention may be built into a ceiling tile or similar structures. In alternative embodiments, the air purifying apparatus may be built into a light fixture, a recessed light or a drop-light. In further alternative embodiments, the air purifying apparatus could be built within or could compliment the structure of the building. While a ceiling tile is disclosed as one of the preferred embodiments, the air purifying device could be included within any structure of a building, including a wall unit, a light fixture, the floor or any other complimentary structure of the room such as a piece of art, statue or the like without departing from the general configuration of the unit. The main purpose of the air purifying apparatus is to act as a complimentary system to the general HVAC system of a building. The place where the unit is installed or mounted is not necessarily critical to the function of the unit.

In some embodiments, the air purifying device comprises at least a second vent, and wherein the baffle further defines at least a second airway between the fan and the second vent, wherein a second UV light source is mounted in the second airway, wherein the second airway accommodates a UV-reflective material in at least a portion of the second airway, and wherein a second UV-screen is attached to the first airway to block UV light from exiting the airway.

Further yet, in some embodiments the UV-reflective material creates a kill zone which decontaminates air flowing through the first and second airways. In some embodiments, a second fan is mounted in the apparatus. Some embodiments include an air diversion mechanism configured to divert air into the first and second airways. The first and second fan can be configured to rotate in opposite directions. The UV light source may be activated and de-activated remotely to decontaminate airflow through the first and second airway. In some embodiments, the UV light source is a UV-C light source having a wavelength between 200 to 280 nanometers.

The present invention further addresses the need to contain the light emitted from a UV-C light source within the chamber to create the kill zone. An extensive system of barriers are utilized within the kill chamber to create a kill zone while precluding the UV-C light from exiting the kill chamber. The baffles may be coated with a reflective material to enhance the effectiveness of UV-C light within the kill chamber.

The present invention combines the benefit of savings in electrical energy with savings in HVAC energy costs in one unit.

The present invention further includes the benefit of adapting the fan and LED lighting fixture to fit into the foot print of a ceiling tile, a light fixture, a wall or other structure to permit installation of the fixture in room configurations, thus maintaining the aesthetics of the room. The placement of the apparatus of the present invention within the building is not critical to the operation, function or nature of the present invention.

The present invention may be mounted on a portable structure that allows for the UV-C light system to be transported within a structure or mounted using a universal mount that provides that the air circulation unit may be placed at various locations within a room.

The present invention also includes the benefit of utilizing an ethernet or Wi-Fi (wireless) connection for remote control of the lighter and fan.

The present invention includes the benefit of moving air in an indoor space to provide more efficient heating of the indoor space.

The present invention may include the stepped fan blade technology of U.S. Pat. Nos. 10,428,831, 10,273,964 and 10,316,141, which are all incorporated herein by references in their entirety. The stepped-fan blade technology provides the benefit of moving air through the fixture in a more efficient manner, thereby reducing the amount of energy required to operate the unit. The stepped blade technology also enables the fan to operate at a lower speed, thus utilizing less energy and reducing noise. Finally, the stepped-fan blade technology disperses the air in a uniform manner.

The present invention provides the additional benefit of enhancing the life of all of the electrical fixtures (both the lighting and fan fixture) by reducing the amount of deterioration on each fixture caused by heat.

The present invention will also enhance the foot-candles' per watt performance of the lighting optics by reducing the temperature of the LED light. The present invention reduces the problem of the LED light degrading over time due to an increase in temperature.

This design of the present invention will also enhance the ability to self-clean the lens on the LED face by utilizing air to push any dust or debris away from the lighting fixture.

This design of the present invention provides for a competitive advantage in that it permits electrical hook up in one complete unit that used to require two separate electrical connections, one for the fan and one for the light.

An added benefit of the present invention provides for a filter to clean the air that comes through the perforations of the intake or the screen of the light fixture-therefore creating a cleaner air environment.

The present invention may utilize various color schemes to impact various behavior traits of a person. Color is believed to profoundly affect the productivity of a person. Research has shown that blue color is believed to affect a person's mind; yellow is believed to affect a person's emotions; red is believed to affect a person's body; and green is believed to affect a person's balance. Utilizing these colors in the present invention, the colors can affect a person's behavior. The colors scheme may be incorporated into the lens, the troffer shelf or the LED light.

Finally, the present invention presents a benefit of elimination of any strobing effect caused by the fan blades interfering with the light distribution.

These and other objects and advantages of the present invention, as well as the details of the illustrative embodiment, will be more fully understood from the following specification and drawings.

DETAILED DESCRIPTION OF THE INVENTION

Figure 1:
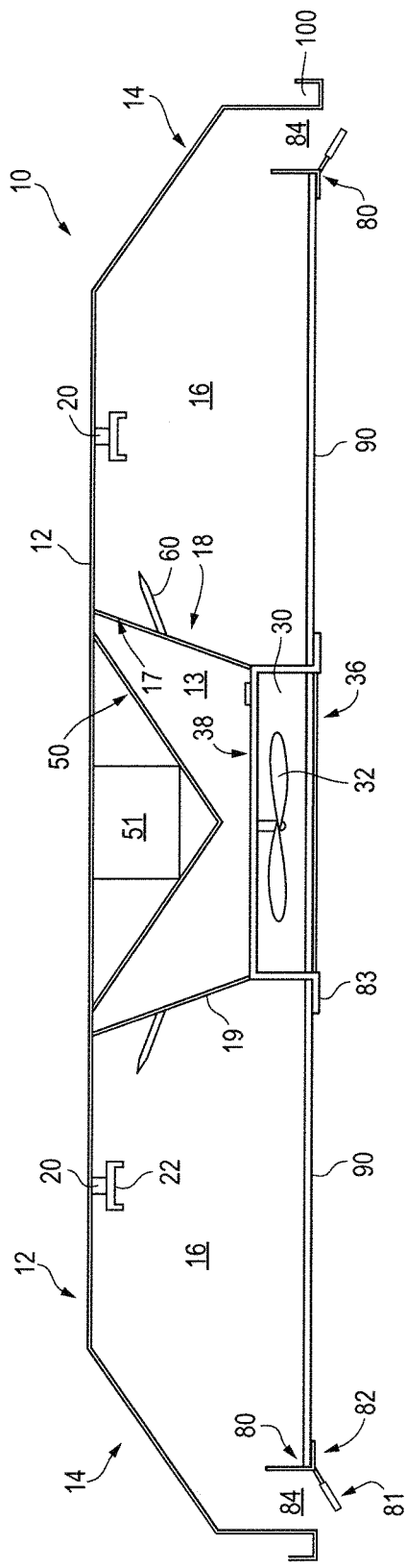
FIG. 1 is a sectional view of one embodiment of the combination light and fan fixture depicting a troffer shelf.
Figure 2:
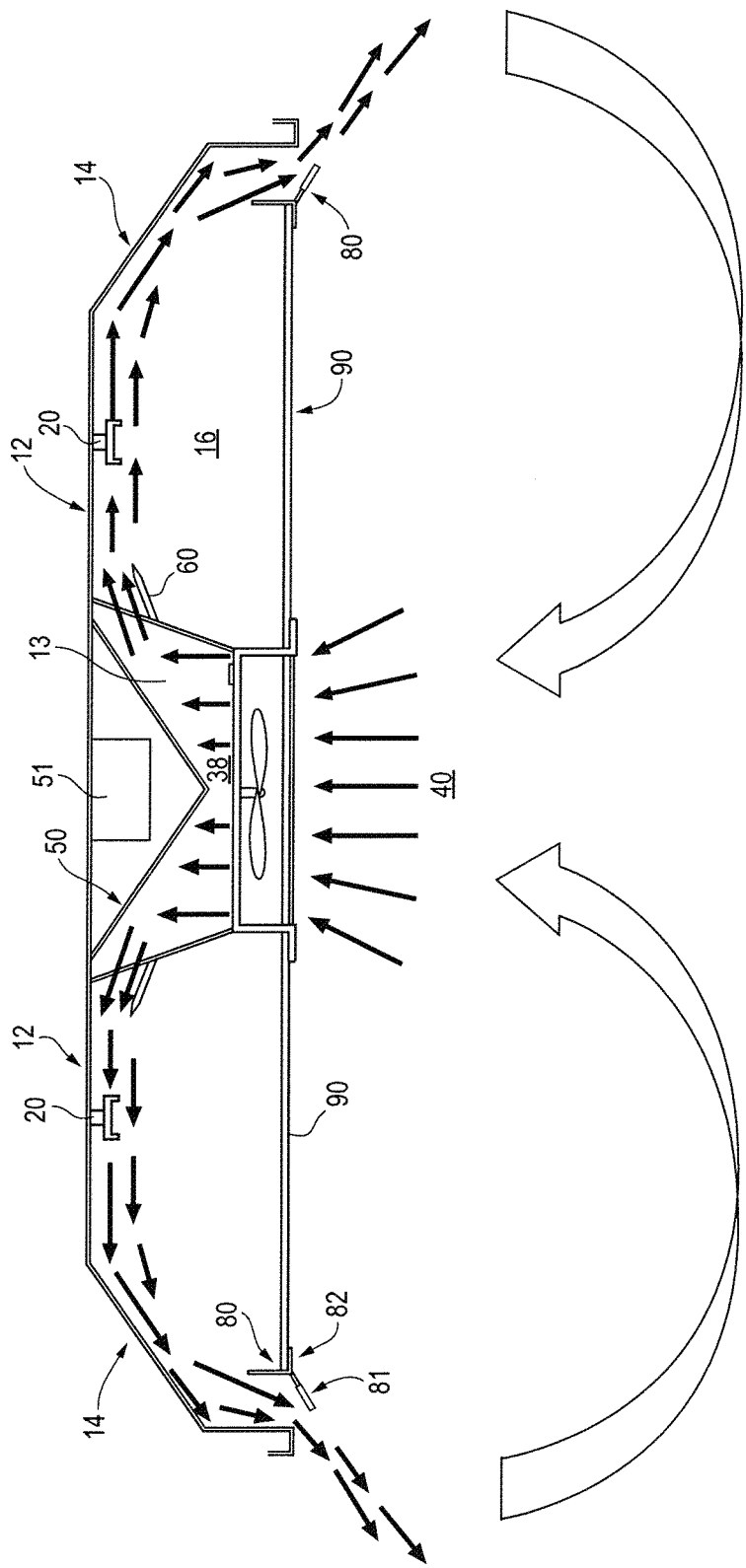
FIG. 2 is a sectional view of one embodiment of the combination light and fan fixture showing the flow of air.
Figure 3:
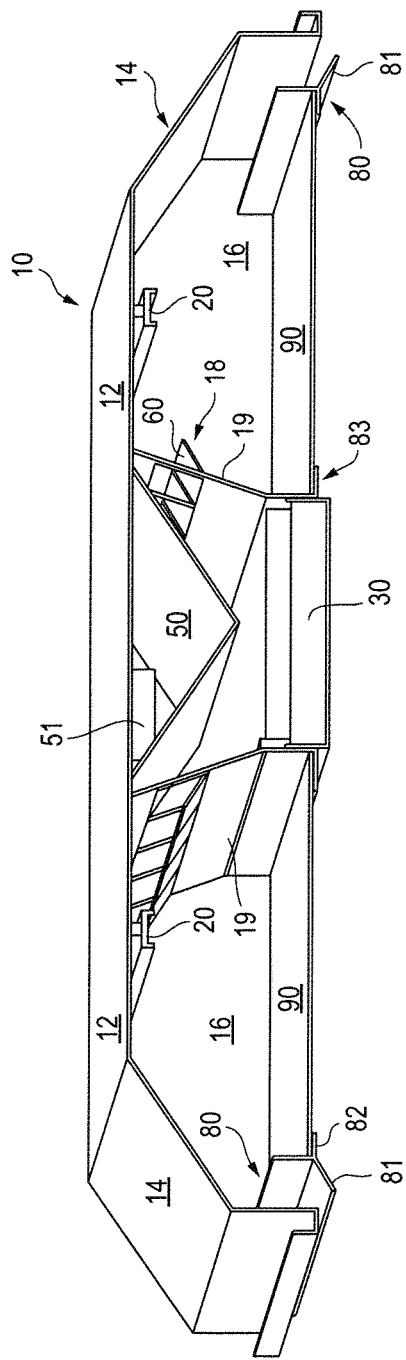
FIG. 3 is a prospective view of one embodiment of the combination light and fan fixture depicting a troffer shelf.

Embodiments of the present invention may comprise a combination of a fan and an LED light fixture. FIGS. 1 and 2 show side sectional views of an embodiment of the present invention depicting a troffer shelf 12. FIG. 3 shows a perspective view of an embodiment having a troffer shelf. The combination fan 10 may include a troffer shelf 12 which supports at least one LED light fixture 20 and a fan 30. The fan 30 is supported by a louvered fan support 18. As shown in FIG. 3, the louvered fan support 18 has a lower solid portion 19 and an upper open portion 17 that includes several opening and louvers 60 which direct air from the fan chamber 13 along the troffer shelf 12. It is not material to the present invention where the solid portion 19 and open portion 17 is located in the fan support 18. What is important is that there is a solid portion 19 of the fan support 18 that braces the fan 30, and an open portion 17 that is configured to permit air to flow from the fan chamber 13 to the troffer chamber 16. The direction of the air flow is not necessarily important to the present invention. What is important is that the fan 30 causes air to flow in the vicinity of an LED light fixture 20.

The troffer shelf 12 may have the same general dimensions as a ceiling tile typically 1 ft.×2 ft., 2 ft.×2 ft. or 2 ft.×4 ft. While the FIGS. 1-22 depict the present invention taking the form of a ceiling tile, dropped lighting fixture or a canned lighting fixture, the present invention could be incorporated into any tile-like structure or lighting fixture incorporated into a building or features within the building. For example, the embodiments of FIGS. 1-22 could easily be incorporated into a wall or floor of a building. It could be positioned within a piece of art or a statue. Additionally, the present invention could be positioned in a light fixture. It does not necessarily matter where the present invention is incorporated into a structure. What is important is that the present invention is self-contained within a troffer shelf 12 or similar housing, and that the system operates to augment or supplement the HVAC system of a building or structure. Therefore, while certain embodiments are disclosed in the form of a ceiling tile or light fixture, the present invention is not limited to the specific structure of a ceiling tile or light fixture. In fact, the present invention could be utilized in a ceiling, a wall unit or floor of a structure without departing from the nature, configuration or operation of the present invention.

The LED light fixture 20 is typically positioned along the troffer chamber 16 along the troffer shelf 20 such that light from the fixture 20 is not interrupted by the fan 30. The LED light fixture may include an LED lamp 22. The LED light fixture 20 is preferably in the form of a strip which runs the length of the troffer shelf 12 or housing. While the term troffer shelf 12 may be used throughout this application, the term also refers to a housing or similar structure. The LED light fixture 20 is secured to the troffer shelf 12 in such a manner to permit air to flow along a substantial portion of the surface area of the LED lamp 22 and LED light fixture 20. The LED light fixture 20 may include a magnetic attachment mechanism to secure the LED light fixture 20 to the troffer shelf 12. The magnetic attachment mechanism serves multiple purposes including the ability to detach the LED light fixture 20 from the troffer shelf 12 in a relatively easy fashion. The magnetic attachment mechanism further serves to provide a space between the LED light fixture 20 and troffer shelf 12 for air to flow through, which increases the surface area of the LED light fixture 20 that contacts the air. The greater the surface area of the LED light fixture 20 that comes in contact with the air flow, the faster and more efficient the temperature reduction of the LED light fixture 20. While LED light fixtures are discussed throughout this disclosure, it is understood that other types of lights may be utilized in the invention and benefit from the features of the invention.

Figure 12:
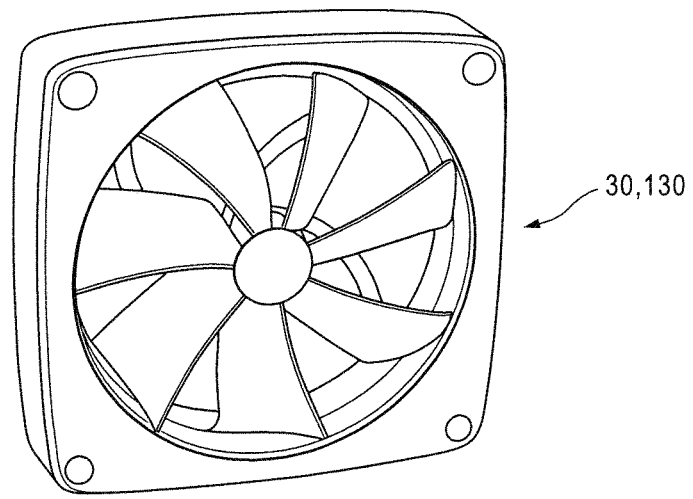
FIG. 12 is a perspective view of an axial fan of the present invention.

The fan 30 preferably includes at least an axial fan as shown in FIG. 12. Referring back to FIGS. 1, 2 and 3, there may be more than one fan within the fan area 13. The blades 32 of the fan 30 force air to move parallel to a shaft 34 about which the blades 32 rotate. Air flow 40 moves axially through the intake of the fan 36 and axially out through the outlet 38 of the fan 30. The flow of air is generally linear trough the intake 36 and the outlet 38. The design of the fan 30 is a function of the blade configuration 32 that creates a pressure of differential that produces airflow 40 across the fan blade 32. The fan 30 may consist of anywhere from 2 to 8 blades. The fan 30 is connected to a motor 51 and typically operates at high speeds. The typical speed of the axial fan of the present invention operates between 1800 to 4000 RPM to produce airflow in the range of 85 to 150 cubic feet per minute. While an axial fan is disclosed in the figures of the invention, it is understood that other types of fans such as a bladeless fan, cross-flow fan or impeller-type fan may be used as the fan 30 in the embodiments shown in the figures. Any of those types of fans can be utilized without having a detrimental effect on the function and features of the invention. The important feature of the fan 30 is to move and distribute air within the fan area, regardless of the type of fan that was used.

As shown in FIG. 2, the configuration of the troffer shelf 12 directs the flow of air from the outlet 38 of the fan 30. Air flows along the troffer shelf 12 and the troffer baffle 14, along the LED light fixture 20. Air passing along the LED light fixture 20 acts to dissipate heat produced by the LED light fixture 20 which reduces the operating temperature of the LED light fixture 20. In essence, the air flow reduces waste heat produced by the LED fixture 20 by conducting the heat away from the LED light fixture 20. It is believed that the airflow in the current invention can reduce the temperature of the LED light fixture 20 from approximately 120° F. to approximately 80° F. in the typical environment found in offices, hospitals, retail stores, educational institutions and the like.

FIGS. 1, 2 and 3 depict a combination LED light fixture 20 and fan 10. The air exiting the outlet 38 of the fan 30 is propelled into the fan chamber 13. The air in the fan chamber 13 as shown in FIG. 3, is directed by a diversion mechanism 50 so that the air flows through openings 17 in the fan support 18. The air flowing through the opening 17 is directed by louvres 60 into the light chamber 16, along the troffer shelf 12, to engage the LED light fixture 20. By directing air from the fan 20 along the troffer shelf 12 causes the air to circulate around the LED light fixture 20 to reduce the temperature of the LED light fixture 20. The air flow in the lighting chamber 16 is directed by the troffer baffle 14 through an exit vent 84 formed by the damper 81.

In embodiments of the present invention, there may be a vent and lens bracket 80. The bracket 80 is affixed to the troffer shelf 12 in such a manner to permit air to flow from the light chamber 16 through an exit vent 84 formed by a damper 81 in the bracket 80. The vent 84 permits the air heated by LED light fixture 20 to exit the light chamber 16. The bracket 80 also includes a lens bracket 82. The lens bracket 82 corresponds with a fan lens bracket 83 to secure a lens 90 in place within the combination LED light and fan 10. The lens 90 provides a solid surface to assist with containing any air from the fan 30 such that it proceeds along the troffer shelf 12 and the troffer baffle 14 to the LED light fixture 20 and through the vent 84. A lens 90 is not necessary to the invention. However, the lens 90 typically made of a somewhat flexible translucent plastic material. There is a mounting mechanism 100 that is used to affix the combination LED light fixture 20 and fan to an adjacent ceiling tile or bracket.

Some embodiments of the present invention may incorporate the use of color displayed by the lighting system to affect the environment in which the combination LED light 20 and fan fixture 10 may be implemented. Research has shown that different colors appear to affect behavioral traits in humans. For example, the color yellow is believed to influence a person's self-confidence; the color red is believed to influence a person's physical body, the color blue is believed to influence a person's mind and the color green is believed to influence a person's emotional balance. It is believed that, for example, the combination of a yellow color with a blue color will stimulate a person's emotional balance and mind. The different color combinations may be incorporated into the present invention in numerous ways. In one embodiment of the present invention, the colors blue, red, yellow or green may be applied to the internal surface of the troffer shelf 12 and/or the troffer baffle 14 by means of paint, insert or other known technique. Alternatively, the lens 90 may comprise of the colors blue, red, yellow or green. The colored lens 90 operates to transmit light of the lens color in an indoor space. Finally, the LED light fixture 20 itself may be configured to generate light in the blue, red, yellow or green spectrums by means of the LED lamp 22.

The air exiting from the fan cavity 16 is directed along an airflow surface on the troffer shelf 12 and troffer baffles 14 air may alternatively be directed through a cooling chamber, which is not shown but functions to cool the fan components, as well as, the LED lighting components. The internal surface of the troffer shelf 12 and troffer baffles 14 may be coated with a Miro-Micro Matt wet paint produced by Alanod. The paint helps to maintain airflow along the surface, as well as, maintain a clean dust-free surface. The airflow 40 has two general components. The air that exits the fan cavity 13 generally has a laminar flow along the airflow surface of the troffer shelf 12. As the flow of air from the fan 30 extends towards the exterior perimeter of the troffer shelf 12 and troffer baffles 14 through the vent 84, the flow becomes more turbulent and mixes with the surrounding air. The preferred direction of the air-flow is such that the intake 36 of the fan 30 draws air from the lower portion of a space and distributes the air along the upper portion of the space. Air along the lower portion of an area tends to be cooler than air that resides at the upper portion of an area. The cooler air is pulled into the fan 30 and distributed from the cavity is used to cool and clean the LED light fixture 20, and/or the LED light bulb 22.

The combination fan of the present invention may utilize the stepped-fan blade design depicted in U.S. Pat. Nos. 10,428,831, 10,273,964 and 10,527,046, each of which is hereby incorporated by reference, in the entirety. The benefits of the stepped-blade design are set-forth in detail in the pending patent applications referenced herein and need not be repeated in this provisional application and are not shown in the drawings. The stepped-fan blade design greatly improves the air flow characteristics of the fan 30.

Figure 9:
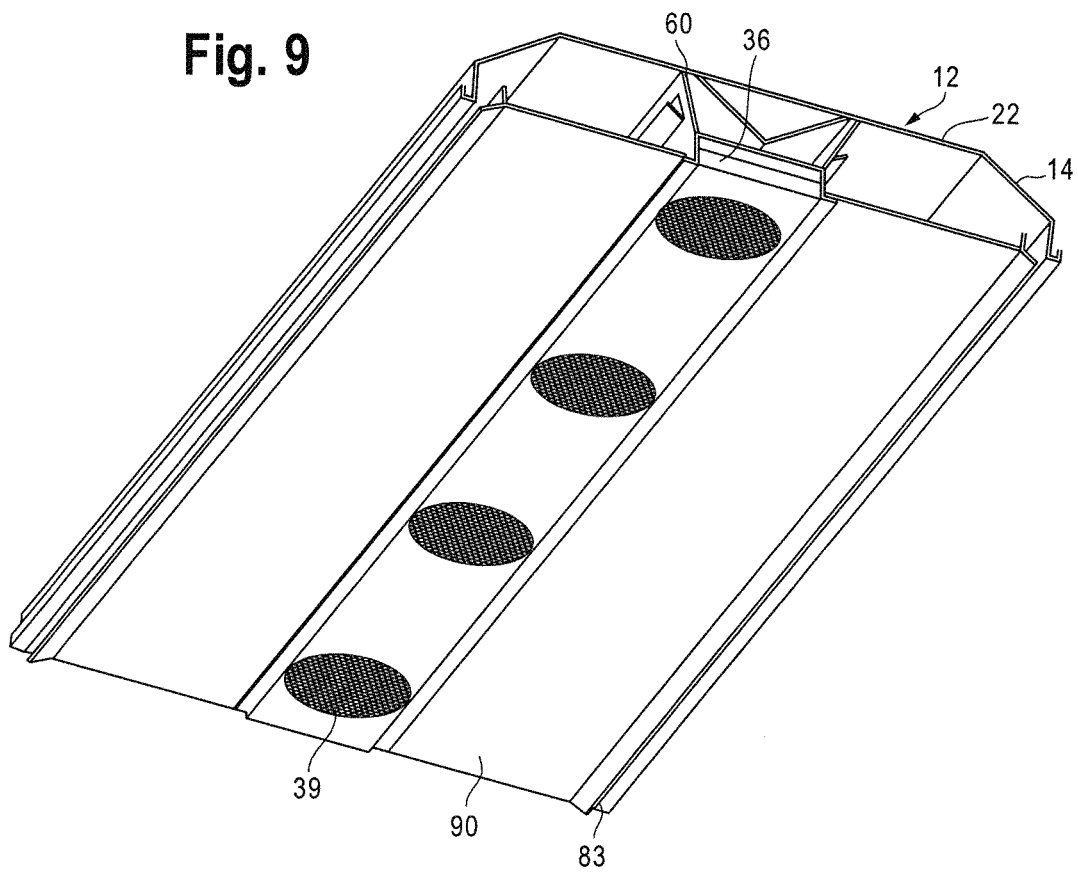
FIG. 9 is a perspective view of an embodiment of the present invention utilizing multiple round grills.
Figure 9A:
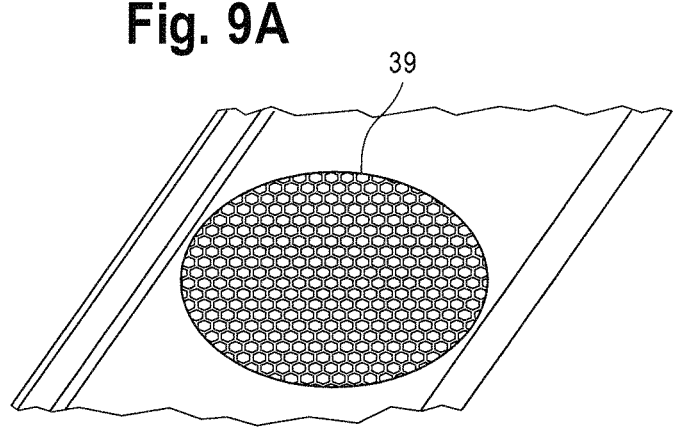
FIG. 9A is a perspective view of the fan grate depicted in FIG. 9.
Figure 10:
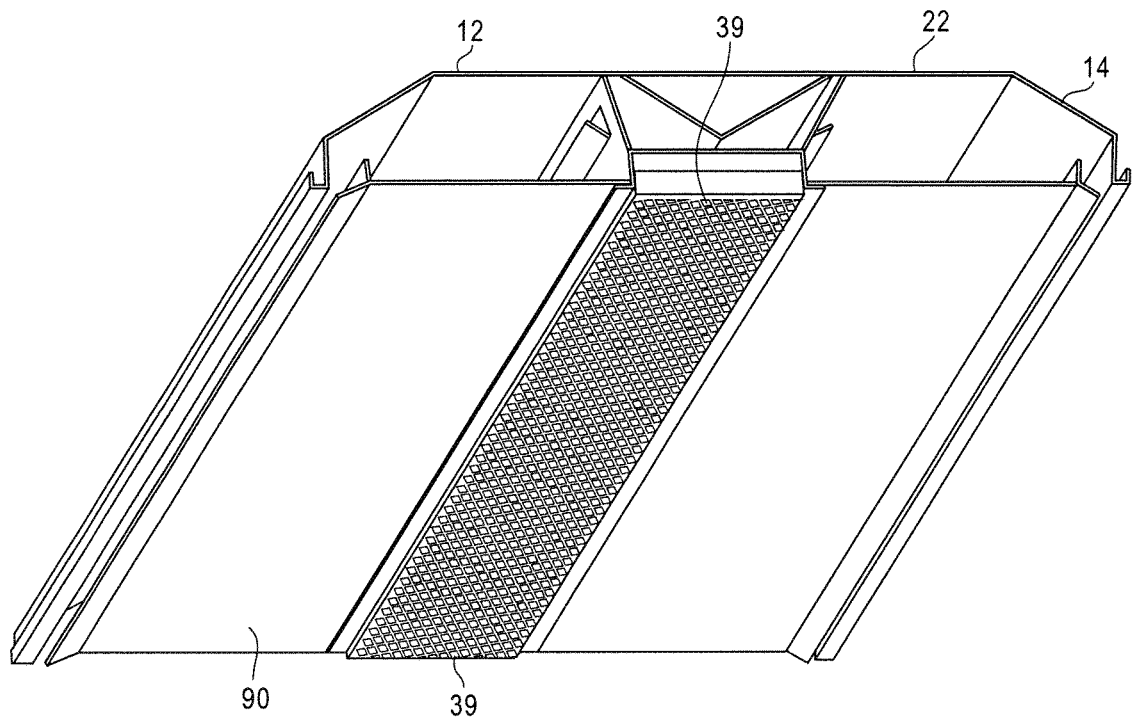
FIG. 10 is a perspective view of an embodiment of the present invention utilizing a single grill and lens.
Figure 10A:
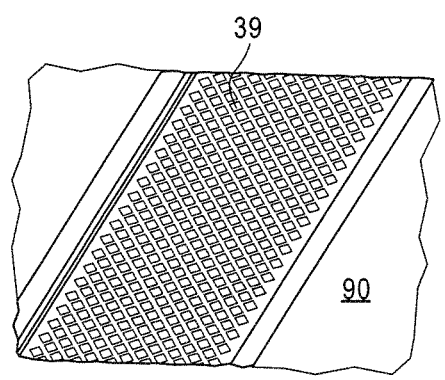
FIG. 10A is a perspective view of the fan grate depicted in FIG. 10.

As shown in FIGS. 9, 9A, 10 and 10A, the fan intake 36 may include decorative perforations and/or a grill 39. The embodiments of FIGS. 9, 9A, 10 and 10A may be installed in a ceiling, wall or floor of a structure without departing from the nature, operation or function of the present invention. The grills 39 may be of a circular configuration as shown in FIGS. 9 and 9A. Alternatively, the grill may extend the length of the fan intake 36 as shown in FIGS. 10 and 10A. The fan intake 36 may also include a filter (not shown). Alternatively, the filter may be positioned at the air outlet 38 or at a grill covering the combination fan 39. The filter serves to clean air flowing through the fan of dust and other fine particles. The filters may be removed for cleaning or replacement on a periodic basis. The embodiments shown in FIGS. 10 and 10A are more adapted to accommodate a filter.

In some embodiments of the inventions, the combination fan and LED light system 20 further includes an air diversion mechanism 50. The air diversion mechanism 50 is positioned within the cavity of the fan chamber 13. The physical configuration of the air diversion mechanism 50 is such that it directs air exiting the fan outlet 38 through the louvered openings 17 or diffuser in the louvered fan holder 18. In some embodiments, the air diversion mechanism 50 is in the shape of a prism as shown in FIGS. 1 through 7. Alternatively, the air diversion mechanism 50 may be in the shape of a pyramid (FIG. 8), cone, pentagon, triangle or other suitable shape to divert air from the fan chamber 13, through the openings 17 and into the troffer chamber 16 along the LED light fixture 20. The air diversion mechanism directs air towards opening 17 along louvered vents 60 positioned along the inside fan chamber 13. The vents 17 may include louvres 60 to assist in directing the air in the desired direction. Positioned within the air diversion mechanism 50 is a ballast housing 51 for LED lighting ballast, drivers and wires. The ballast housing 51 houses the wiring for both the LED lighting system and the fan to allow for a single hook-up to the electrical outlets or connections positioned within the ceiling.

The air exiting from the fan cavity 13 is directed along an airflow troffer shelf 12 to the troffer baffle 14. Air may alternatively be directed through a cooling chamber, which is not shown, but functions to cool the components located in the ballast housing 51, as well as, the LED lighting components.

As shown in FIG. 2, air 40 enters the fan 30 and is expelled by the fan blades 32 into the air chamber 13. Air flow in the fan chamber is generally laminar. Air is forced into the air chamber 13 and is directed by a louvre 60 through an opening in the fan chamber 13 into the light chamber 16. The air (shown in arrows) has generally a laminar flow along the troffer shelf 12 and troffer baffle 14. As the flow of air from the fan 30 extends towards the exterior perimeter of the housing in the vent 84, the flow becomes more turbulent and mixes with the surrounding air such that the air exiting through the damper 81 is more turbulent in nature. The preferred direction of the air-flow is such that the intake 36 of the fan 30 draws air from the lower portion of a space and distributes the air along the upper portion of the space. Air along the lower portion of an area tends to be cooler than air that resides at the upper portion of an area. The cooler air is pulled into the fan 30 and distributed from the cavity is used to cool and clean the LED light fixture 20, the LED cover 24 and/or the LED light bulb 22. In an alternative embodiment, the direction of the airflow may be reversed.

Turning to FIGS. 4, 5, 6 and 7, refer to alternative embodiments to the embodiment of FIGS. 1, 2 and 3. An alternative embodiment comprises a combination of a fan 30 and LED light fixture 20. FIGS. 4, 5, 6 and 7 show views of different embodiments of the present invention. The embodiments may be incorporated into a ceiling, wall, floor or accessory structure of a room.

Figure 4:
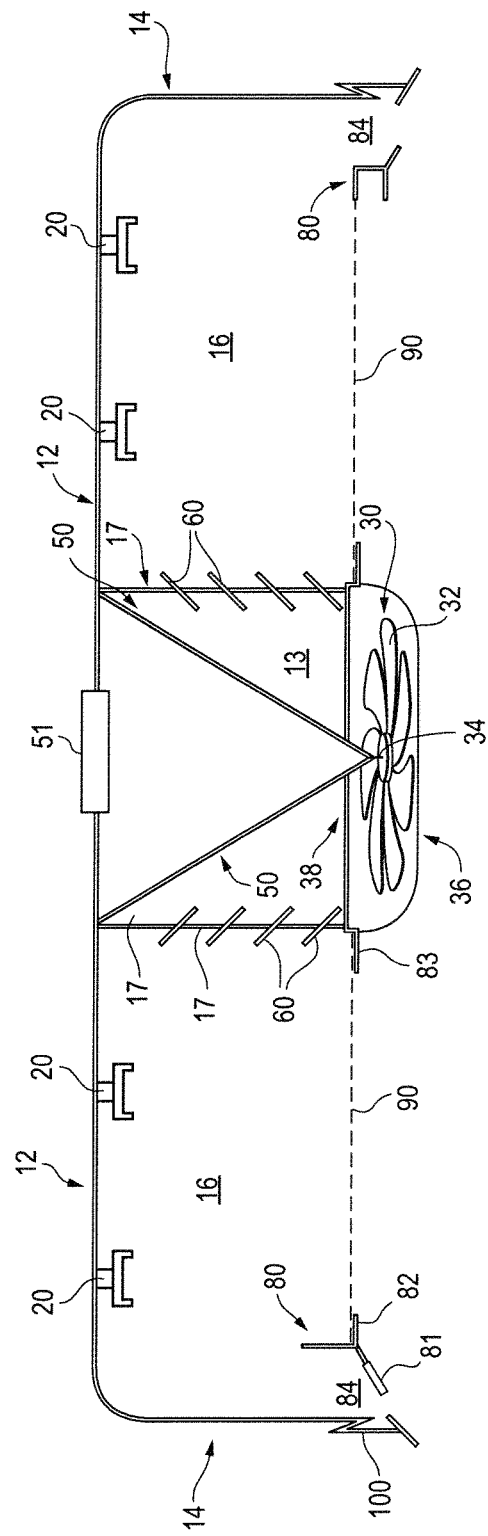
FIG. 4 is a sectional view of one embodiment of the combination light and fan fixture of another embodiment depicting an alternative embodiment of a troffer shelf.

FIG. 4 depicts an alternative design of the troffer shelf and the troffer baffle 14. In the alternative design, air is propelled from the fan 30 into the fan chamber 13. The air from the fan 30 is deflected by a diversion mechanism 50, through the opening 17 and directed by louvres 60 into the light chamber 16. The louvres 60 are configured to direct the air from the fan along the troffer shelf 12 and along the troffer baffles 14. By directing air from the fan 30 along the troffer shelf 12 causes the air to circulate along LED light fixtures 20. The air flow helps to reduce the temperature of the LED light fixture 20. The air flow is directed by the troffer baffle 14 through an exit vent 84 formed by the damper 81, in the lens bracket 80.

In FIG. 4, the troffer shelf 12 has more of a squared-shape. The troffer shelf 12 and the troffer baffle 14 intersect at generally right angles to each other. The fan 30 is positioned in generally the same position as demonstrated in FIG. 3.

The fan chamber 13 includes a diverter 50 to direct air exiting the fan 30 through the open portion 17 of the fan chamber 13. Louvers 60 direct the air passing through the open portion 17 of the fan chamber 30 into the light chamber 16. Air flows along the troffer shelf 12 and the troffer baffle 14 passed the LED light fixture 20. Air passing along the light fixture passes along the plurality of LED light fixture 20 to dissipate the heat in the LED light fixture 20. The air follows a path along the air baffle through the vent 84 out of the light chamber 16.

The bracket 80 includes a damper 81 and lens bracket 82. The embodiment includes a lens 90 which acts to diffuse the light emitted from the LED lights. There is a mounting mechanism 100 used to affix the combination LED light fixture 20 and fan to an adjacent ceiling tile or bracket.

The interior surface of the troffer shelf 12 and troffer baffle 114 may be coated with a Miro-Micro Matt wet paint produced by Alanod. The paint helps to maintain airflow along the surface, as well as, maintain a clean dust-free surface. The paint can be applied in any of the colors discussed above to affect the environment.

Figure 5:
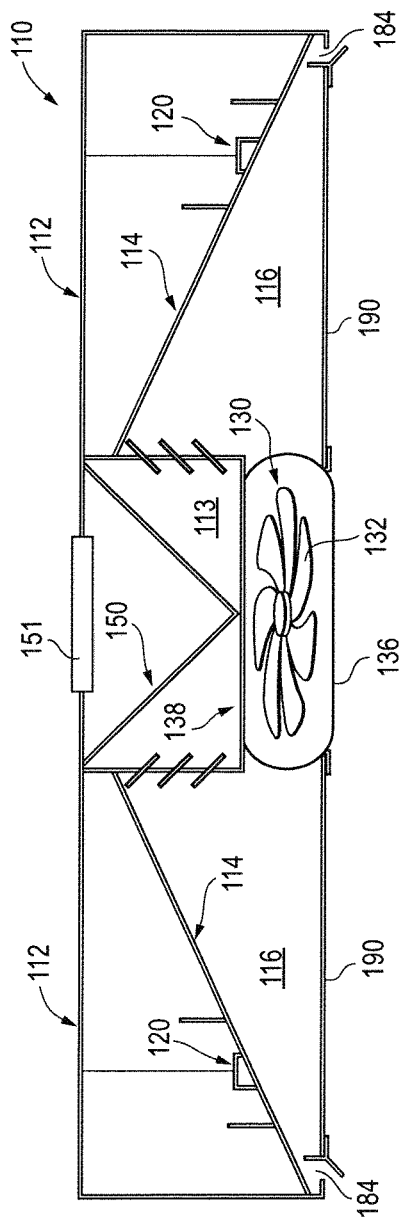
FIG. 5 is a sectional view of one embodiment of the combination light and fan fixture depicting an angled shell showing the flow of air.
Figure 6:
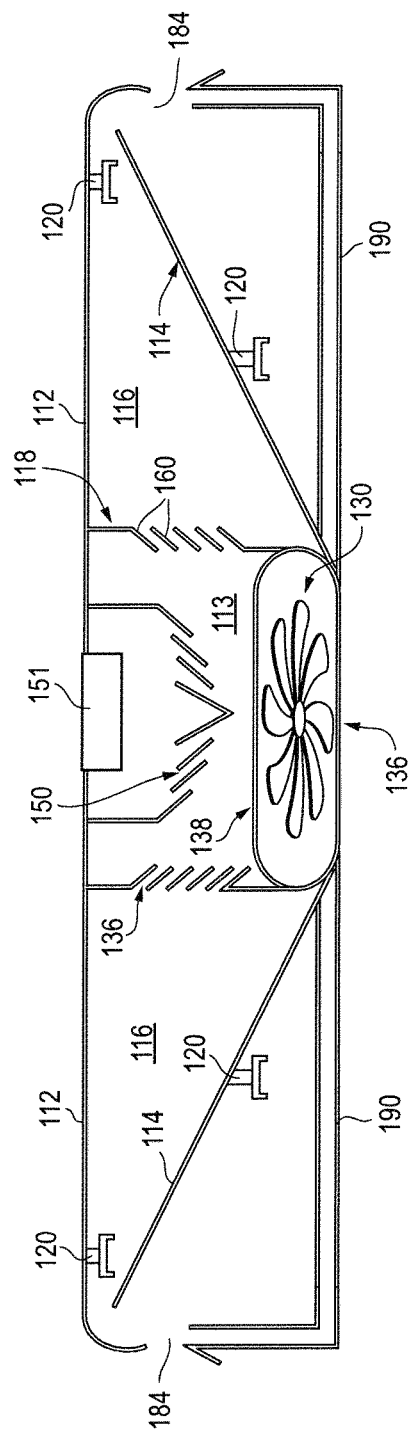
FIG. 6 is a sectional view of an alternative embodiment of the combination light and fan fixture depicting another embodiment of the angled deflection mechanism.

As shown in FIGS. 5 and 6, the combination fan 110 includes a housing 112 which supports at least one LED light fixture 120 and a fan 130. The housing may be the same dimensions as a ceiling tile typically 2 ft.×2 ft. or 2 ft.×4 ft. The LED light fixture 120 is preferably positioned along the periphery of the housing 112 such that light from the fixture 120 is not interrupted by the fan 130. The LED light fixture includes an LED light bulb 122.

The alternative embodiments of the combination LED light fixture and fan 110 utilize an internal baffle 114. The internal baffle 114 serves to direct air within the troffer cavity 116 and provide support for the LED lighting 120. The embodiments depicted in FIGS. 5 and 6 include a fan 130 that directs air through a fan exit 138 in the fan chamber 113. The fan chamber 113 includes an air diverter 150 which may take on many different shapes, such as a prism shown in FIG. 5 or a trapezoidal shape shown in FIG. 6. Air from the fan chamber 113 is directed by the diverter 150 through the open portion 117 of the fan support 118. The air flowing through the open portion 117 of the fan support 118 is directed by louvres 160. As shown in FIG. 6, the air is directed by the louvres 160 into the baffle chamber 116 along the baffle 114 across the LED light 120. The air passing across the LED light 120 is directed by the baffle 114 through the exit vent 184.

In FIG. 5, the baffle 114 guides air flowing through the openings 117 in the fan chamber 113 (which is directed by the baffles) along the LED light fixture 120. The air serves to reduce the temperature of the LED light fixture 120 and extend the life of the LED light fixture 120. The baffle 114 guides the air flow from the LED light fixture 120 through the exit vent 184.

The fan 130 preferably includes an axial fan. The blades 132 of the axial fan force air to move parallel to a shaft 134 about which the blades 132 rotate. The flow of air 140 is axially through the intake of the fan 136 and axially out through the outlet 138 of the fan 130. The flow of air is linear trough the intake 136 and the outlet 138. The design of the fan 130 is a function of the blade configuration 132 that creates a pressure of differential that produces airflow 140 across the fan blade 132. The axial fan 130 may consist of anywhere from 2 to 8 blades. The axial fan 130 is connected to an energy source (not shown) and typically operates at high speeds. The typical speed of the axial fan of the present invention operates between 1800 to 4000 RPM to produce airflow in the range of 85 to 150 cubic feet per minute. The combination fan 142 of the present invention may utilize the stepped-fan blade design depicted in the pending patent applications referenced above.

The fan intake 136 of FIGS. 5 and 6 may include decorative perforations and/or a grill as shown in FIGS. 9 and 10. The air intake 136 may also include a filter (not shown). Alternatively, the filter may be positioned at the air outlet 138 or at a screen covering the combination fan 142. The filter serves to clean air flowing through the fan of dust and other fine particles.

Figure 13:
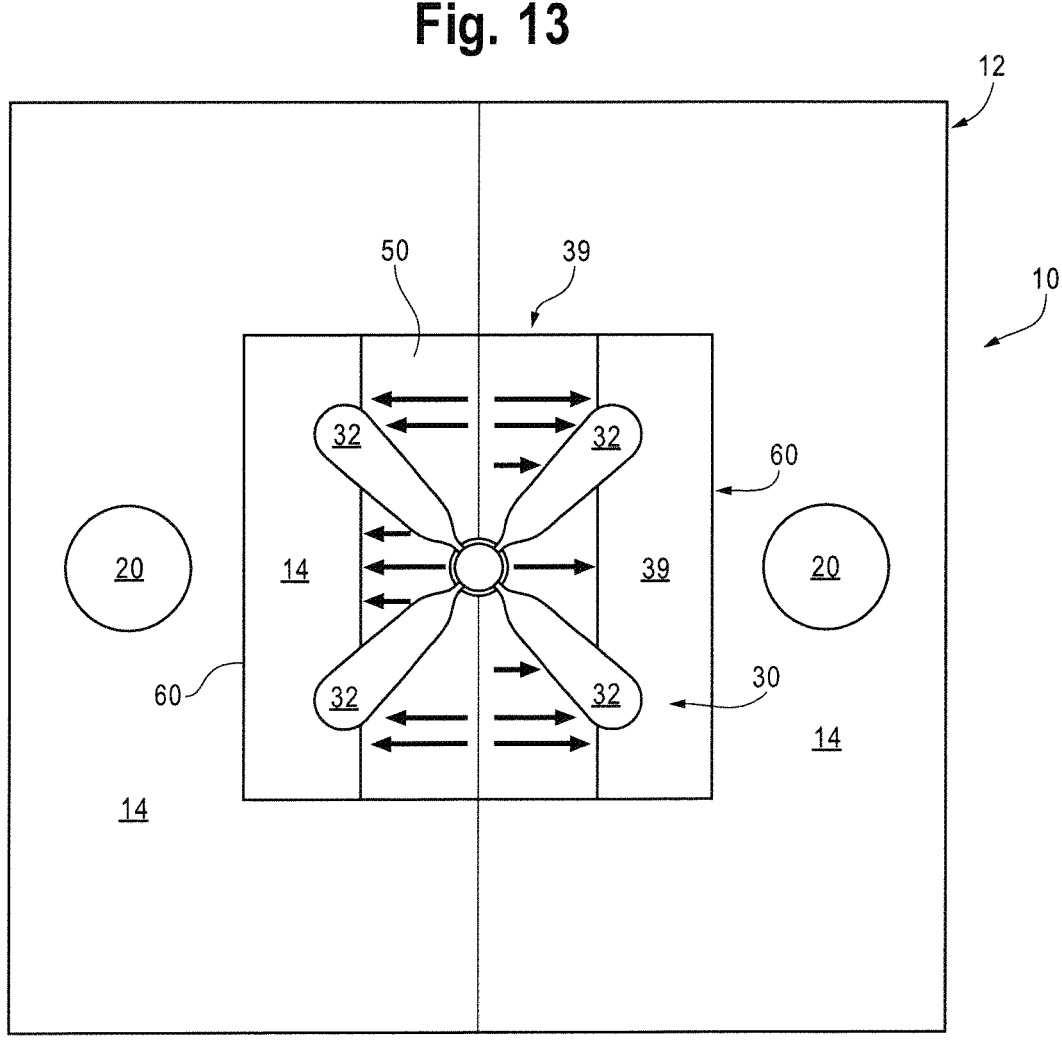
FIG. 13 is a bottom view of one embodiment of the combination light and fan fixture.
Figure 14:
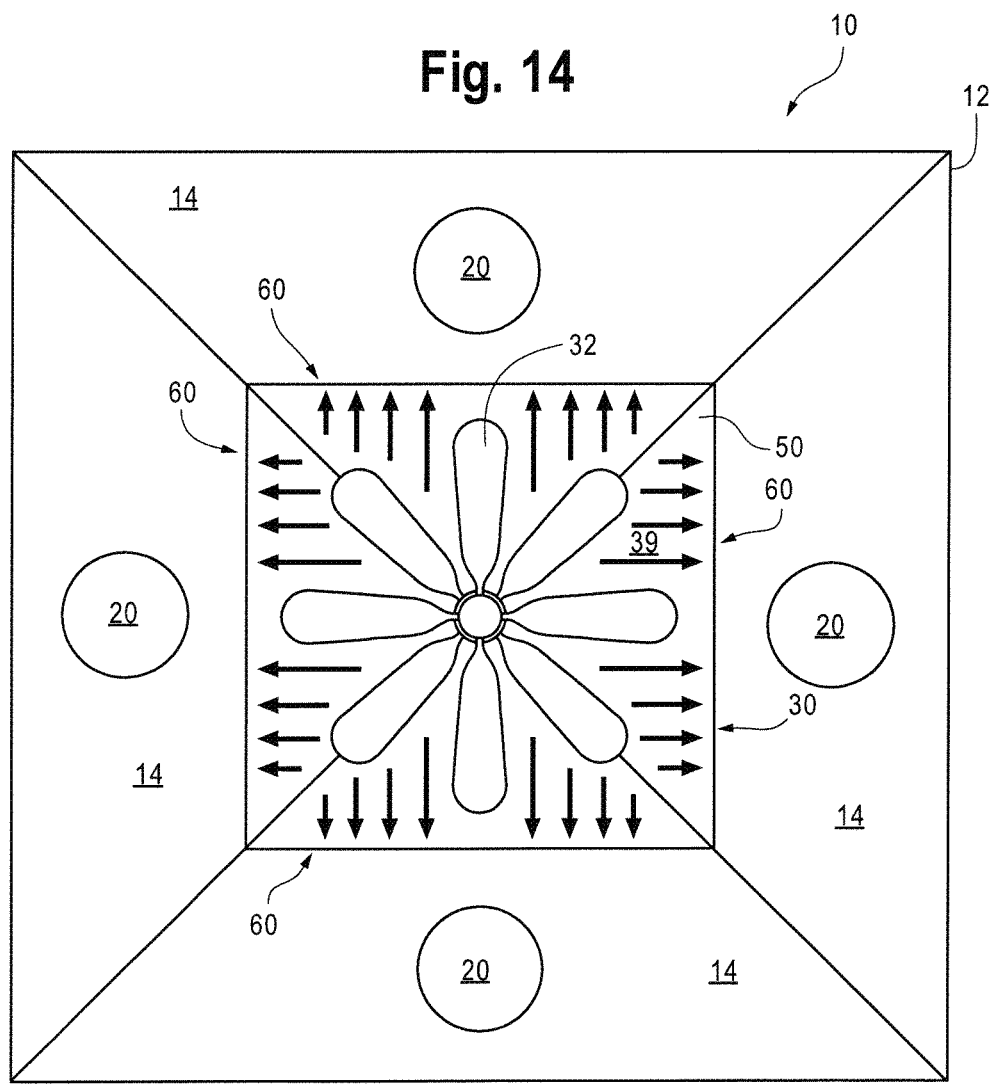
FIG. 14 is a bottom view of an alternative combination light and fan fixture having 4 LED lights.

One embodiment of the combination fan and LED light system 110 further includes an air diversion mechanism 150. The air diversion mechanism 150 is positioned within the fan chamber 113 of the fan 130. Looking at FIG. 14, the air diversion mechanism 150 is in the shape of a prism as shown in FIGS. 5, 6 and 13. Alternatively, the air diversion mechanism 150 may be in the shape of a pyramid (FIG. 14), cone, pentagon, triangle or other suitable shape to divert air to the LED components and into the office space. The air diversion mechanism 150 directs air towards vents 117 positioned along the fan cavity 113. The vents 117 may include louvres 160 to assist in directing the air in the desired direction. Additionally, the air diversion mechanism may have vents to permit a portion of the air circulated by the fan to enter the diversion mechanism 150 to provide a cooling effect on the ballast housing 151.

The air exiting from the fan cavity 116 is directed along an airflow surface on the troffer baffle 114 air may alternatively be directed through a cooling chamber, which is not shown but functions to cool the fan components, as well as, the LED lighting components. The internal surface of the troffer baffle 114 is preferably coated with a Miro-Micro Matt wet paint produced by Alanod. The paint helps to maintain airflow along the surface, as well as, maintain a clean dust-free surface. The airflow 140 has two general components. The air that exits the fan cavity 113 generally has a laminar flow along the airflow surface of the lower housing portion 114. As the flow of air from the fan 130 extends towards the exterior perimeter of the housing 112 through the vent 184, the flow becomes more turbulent and mixes with the surrounding air. The preferred direction of the air-flow is such that the intake 136 of the fan 130 draws air from the lower portion of a space and distributes the air along the upper portion of the space. Air along the lower portion of an area tends to be cooler than air that resides at the upper portion of an area. The cooler air is pulled into the fan 130 and distributed from the chamber where the air functions to cool and clean the LED light fixture 120, and/or the LED light bulb 122.

Figure 7:
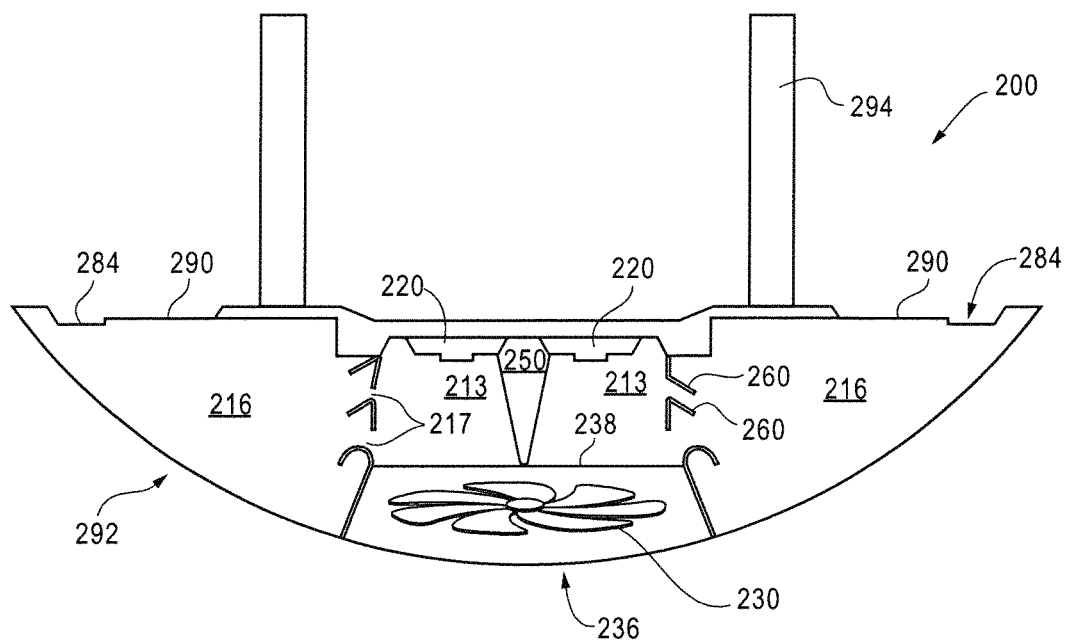
FIG. 7 is a sectional view of yet another alternative embodiment of the combination light and fan fixture with the LED lighting fixture positioned in a dropped indirect lighting configuration.
Figure 8:
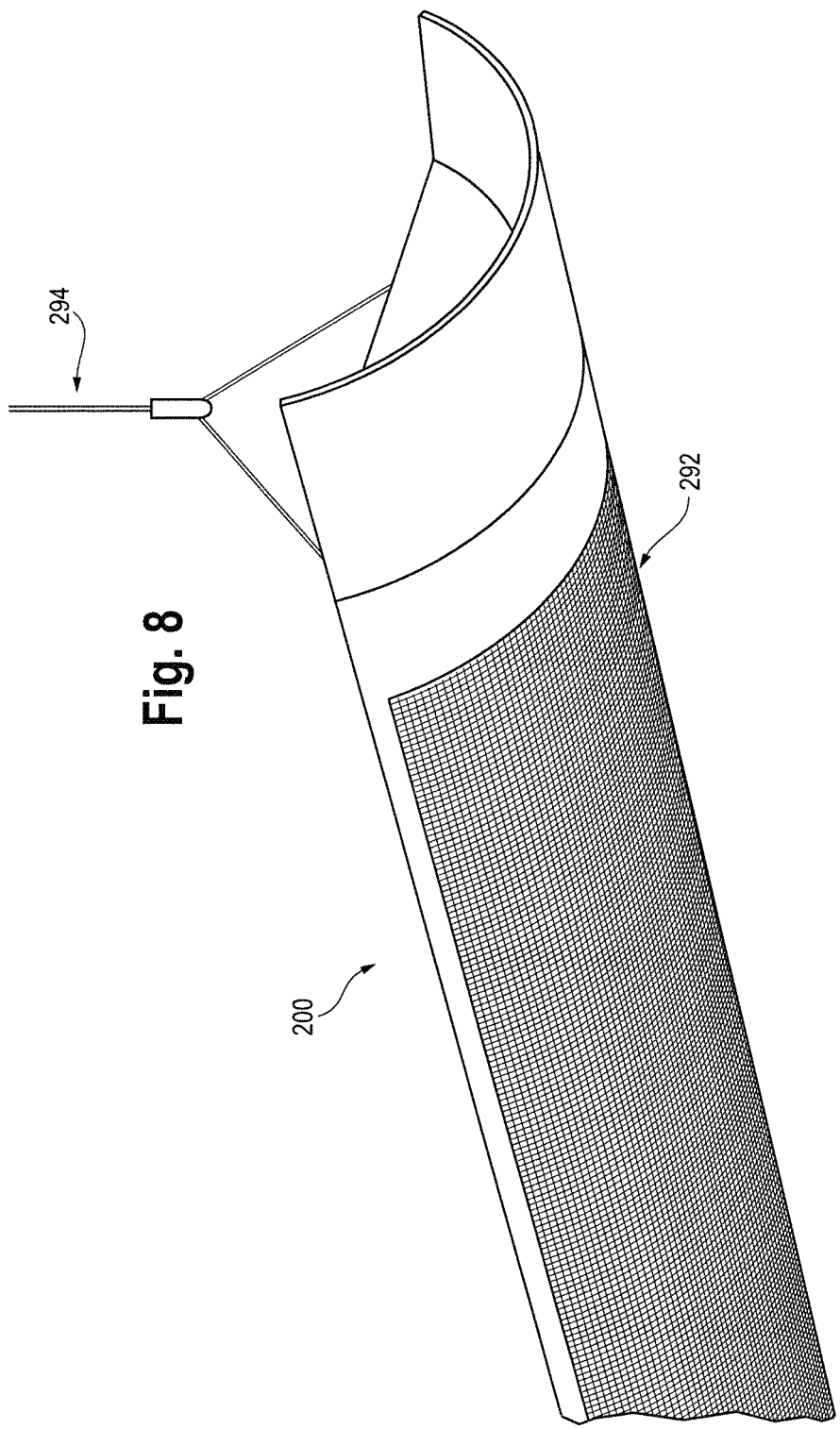
FIG. 8 is a perspective view of the embodiment shown in FIG. 7.

An embodiment of the combination LED light fixture and fan 200 in which the LED light fixtures 220 are directed toward the ceiling is depicted in FIGS. 7 and 8. The combination LED light fixture and fan 200 in FIG. 7 includes a fan 220. The fan 230 may include an invented axial fan, or any fan that serves the purpose of distributing air in a relatively quiet fashion. The fan 230 includes an air inlet 236 and air exit 238. There is a fan chamber 216. Air is drawn from the indoor environment, through the air inlet 236 and propelled by the fan through the fan exit 238 into the fan chamber 213. There is a diverter 250 positioned within the fan chamber 213 to direct air from the fan through an open portion 117 of the fan support 218. The open portion 217 may include louvers 260 to guide the air from the fan chamber 213 into a troffer cavity 216.

The combination LED light fixture and fan 210 has a domed shell 292. While a domed-shaped shell 292 is shown in some embodiments, any shaped shell may be utilized and still practice the invention. The shell 292 serves as a troffer or housing. The shell 292 is configured to direct air from the troffer cavity 216 along the LED light fixtures 220 and through the exit vent 284. A lens 290 is positioned on top of the shell 292. The combination LED light fixtures 220 may be configured to direct light upward toward the ceiling or downward toward the shell 292. The shell 292 may be made of a solid material or alternatively a translucent material to permit light to penetrate the shell 292 into the room. The combination LED light fixture 220 is supported from the ceiling by one or more mounting cables 294. The mounting cables 294 may be configured to accommodate power cables to supply power to the fan 230 and LED light fixtures 220.

The combination LED light fixture and fan as shown in all the embodiments of the present invention may use a hard-wired control mechanism to control both the light 20 and fan 30. The invention may use an ethernet connection and remote control to activate the fan 30 and LED light fixture 20. Alternatively, a wi-fi (wireless) connection may be used in connection with a remote control to control the LED light 20 and fan 30. The remote control feature is configured to adjust the intensity (or color) of the LED light fixture 20 and the speed of the fan 30.

The embodiments of the inventions shown in FIGS. 1 through 7 show a fan that is independent from the HVAC system of the building in which the combination LED lighting fixture 10 may be installed.

Figure 11:
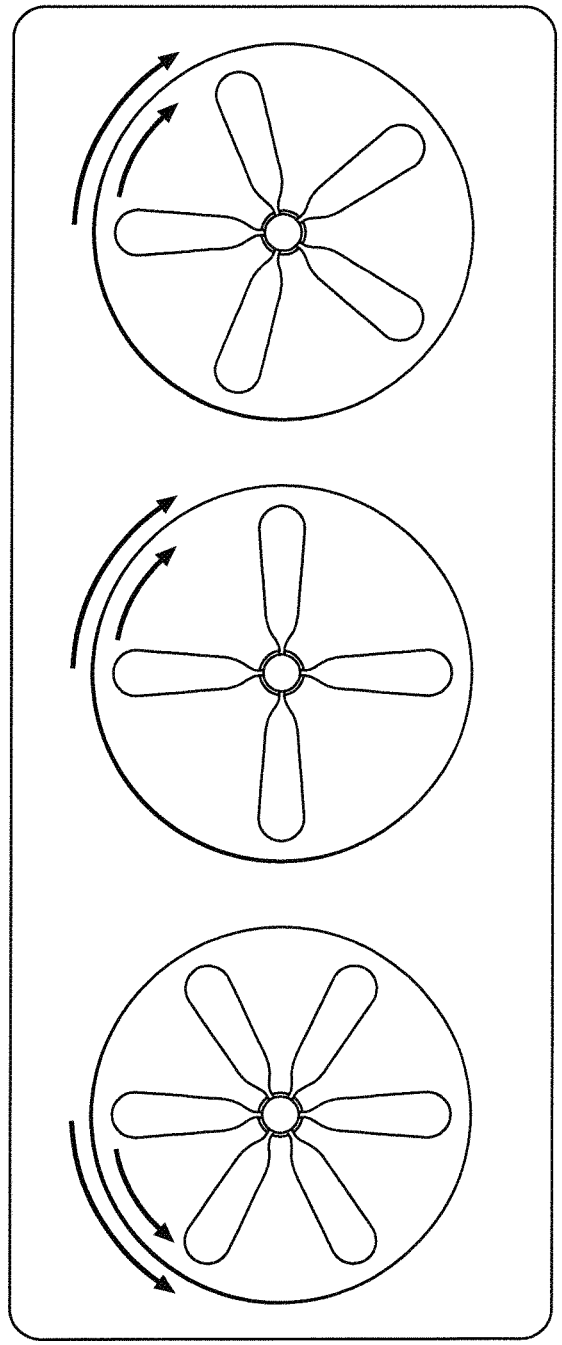
FIG. 11 is a view of the present invention incorporating multiple fan blades.
Figure 11A:
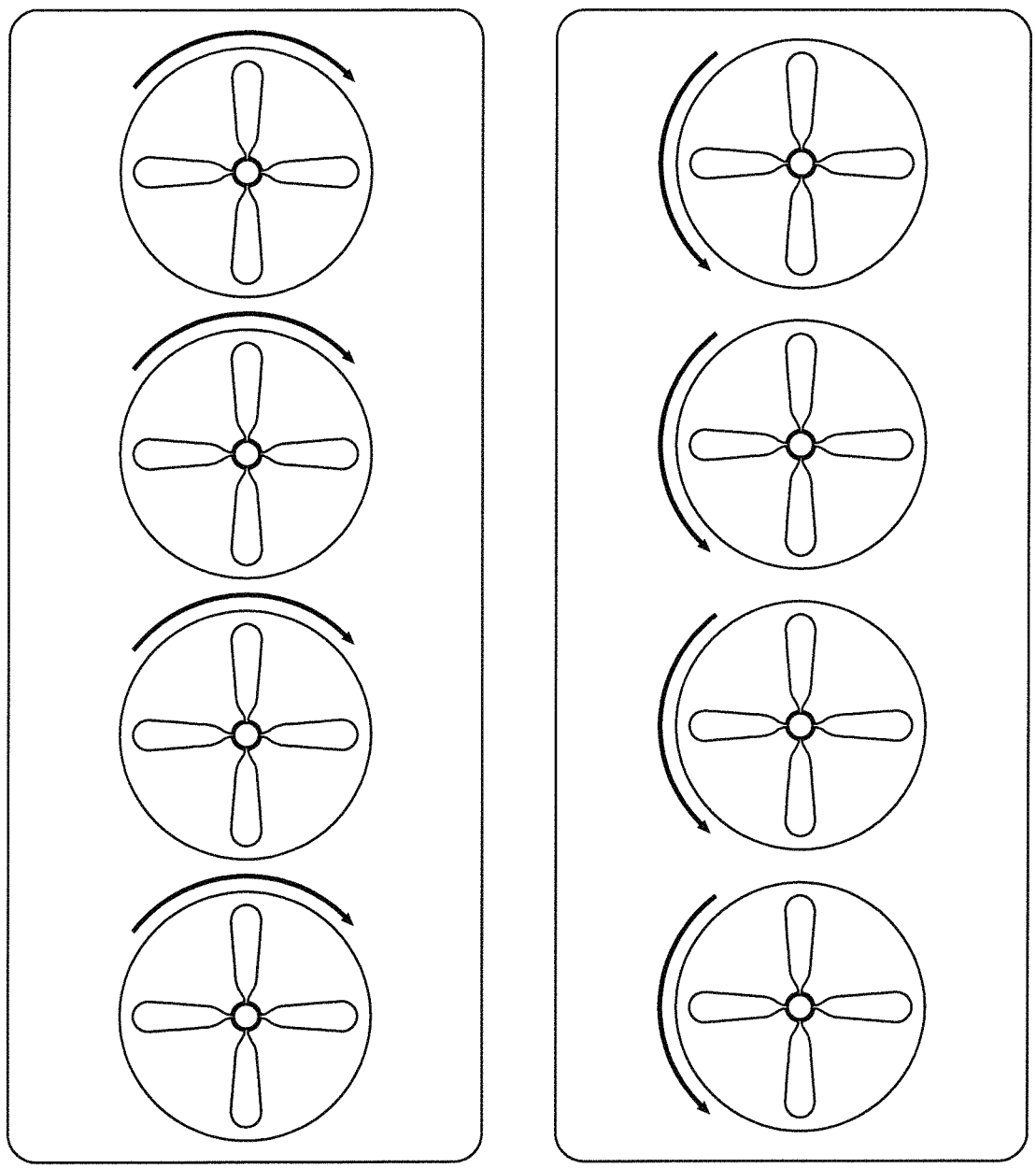
FIG. 11A is a view of the present invention incorporating multiple fan blades.

As shown in FIGS. 11 and 11A, the combination fan may include two or more fans 30. In the multiple fan configuration, it is beneficial that adjacent fans rotate in different directions to provide a more even distribution of air along the fan 30. It is important to note that the adjacent fans rotate in opposite directions. As shown in FIG. 11A, the multiple fans may all rotate in the same direction.

FIG. 12 depicts a fan 30 and 130 that may be used in embodiments of the inventions.

Figure 15:
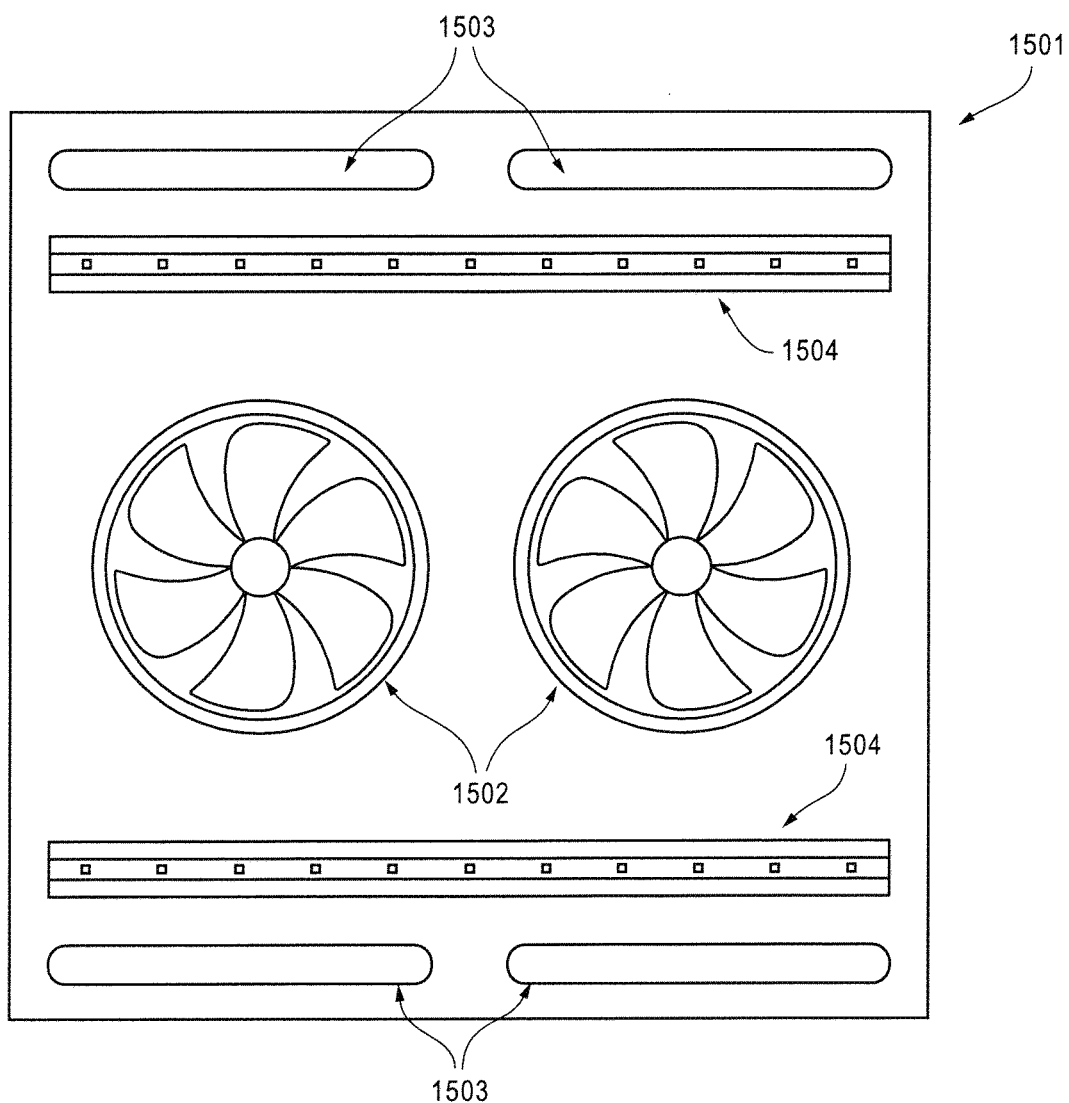
FIG. 15 is a bottom view of a ceiling tile, wall tile, or floor tile having intake fans, exhaust vents, and LED lighting.
Figure 22:
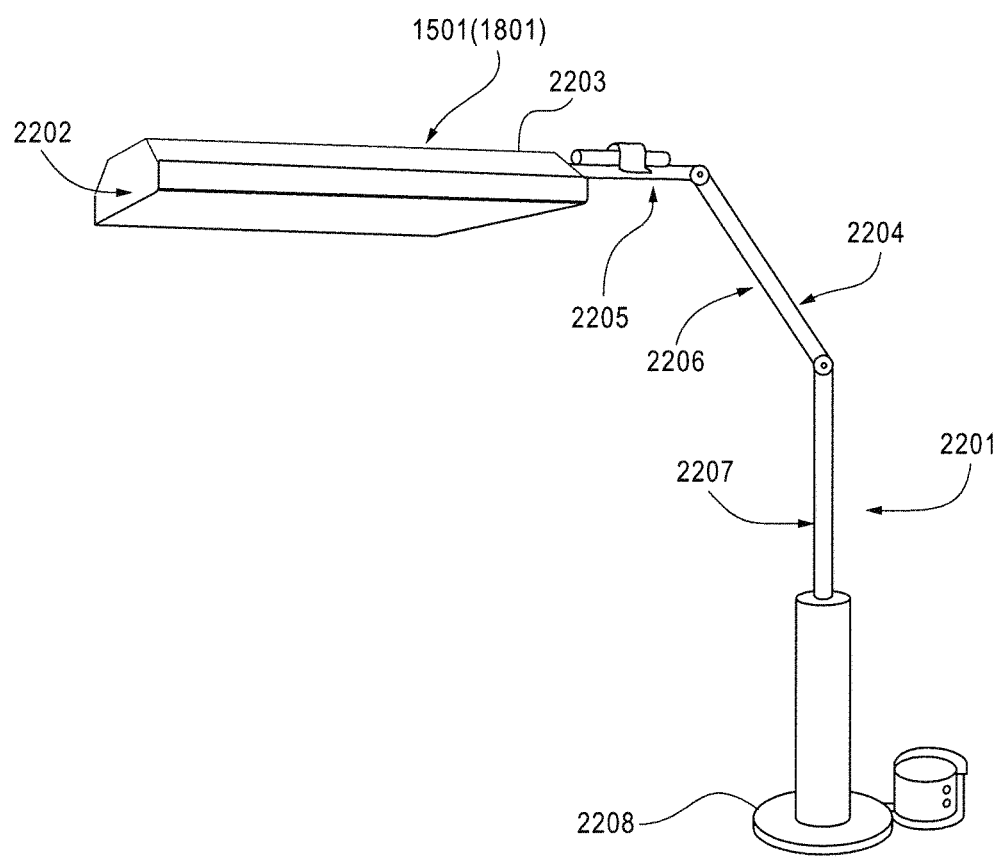
FIG. 22 is a perspective view of the air purifying apparatus of the present invention affixed to a universal mounting mechanism.
Figure 23:
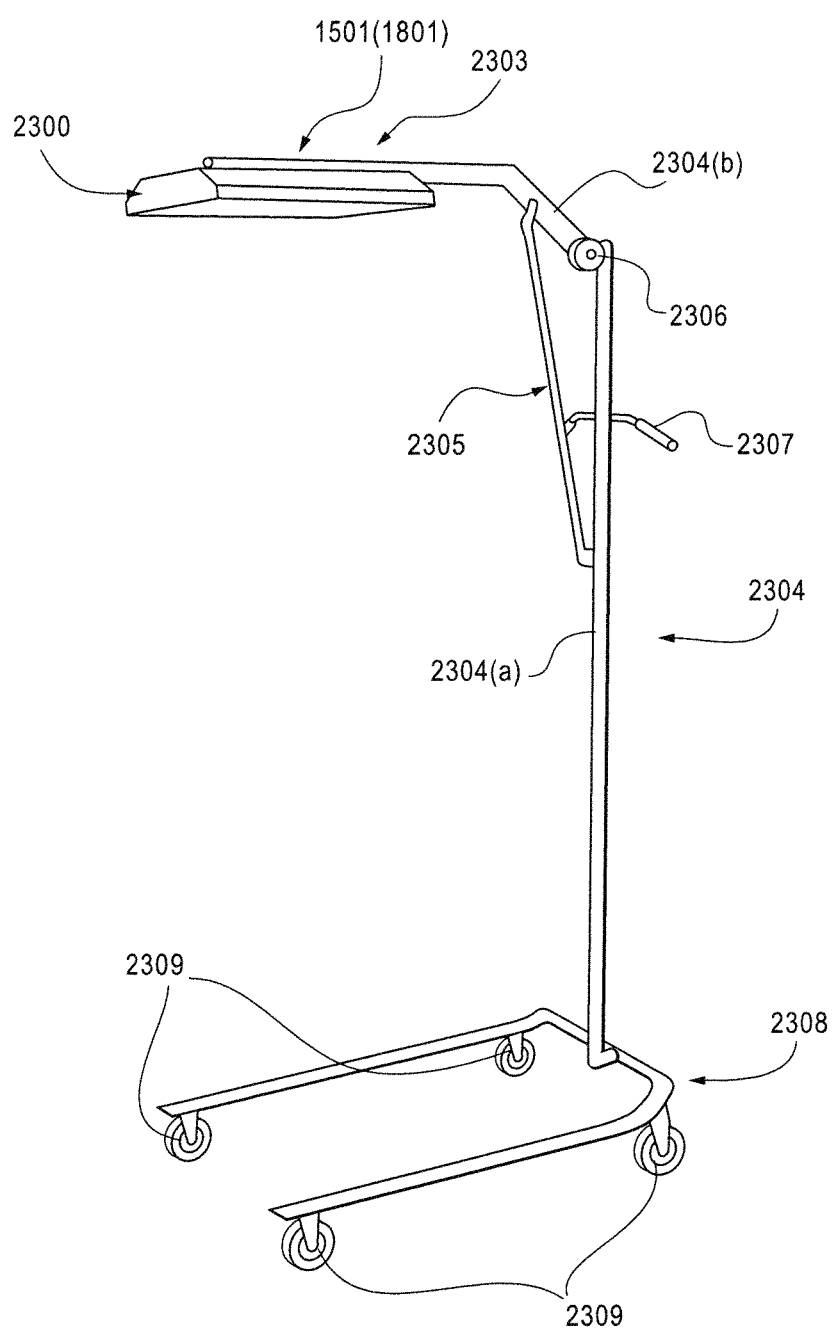
FIG. 23 is a perspective view of the air purifying apparatus of the present invention affixed to a mobile support unit.

Various aspects of this disclosure may include components which are implemented directly into a ceiling grid, ceiling tile, a wall unit, a separate ornate structure or a floor, as seen for example in FIG. 15. It is contemplated that an exemplary UV-C unit 1501 may be sized as 1'×4'; 2'×2'; or 2'×4', although a person of skill in the art would understand that any appropriately sized ceiling tile may be used in accordance with the present inventions. Likewise, a person of ordinary skill in the art would recognize that the exemplary UV-C unit 1501 could be sized to fit between wall joists when it is implemented in a wall or between floor joists when it is incorporated in a floor structure. The UV-C unit 1501 could also be installed in an ornamental piece of such as wall art, statue or installation. Moreover, the UV-C unit 1501 could be constructed of acoustical material, Styrofoam, fiber, wood, metal, translucent plexiglass, plastic, sheet rock or drywall structures as are known to be used in industrial, commercial or residential environments. In essence, the unit could be installed in a ceiling wall or floor without departing from the nature and spirit of the invention. It is further contemplated that the UV-C unit 1501 could be mounted on either a universal mounting mechanism or it could be mounted on a mobile support as shown in FIGS. 22 and 23.

In embodiments of the inventions, UV-C unit 1501 may have one or more fans 1502 and vents 1503 cut into the UV-C unit 1501. Panel cuts may be made or manufactured using waterjet cutting, die cutting, laser cutting, CNC routing, CNC knife cutting, reciprocated knife cutting or any other known techniques for cutting through tiles. Vents 1503 may take the form of elongated slot(s) extending near the edge of UV-C unit 1501, although other shapes are also contemplated. For example, FIG. 15 shows two elongated vents on the UV-C unit 1501's top edge, and two additional vents along the bottom edge. A person of skill in the art would understand that additional arrangements are contemplated. Optional LED strips 1504 may be included and may extend between the one or more fans 1502 and vents 1503.

Figure 16A:
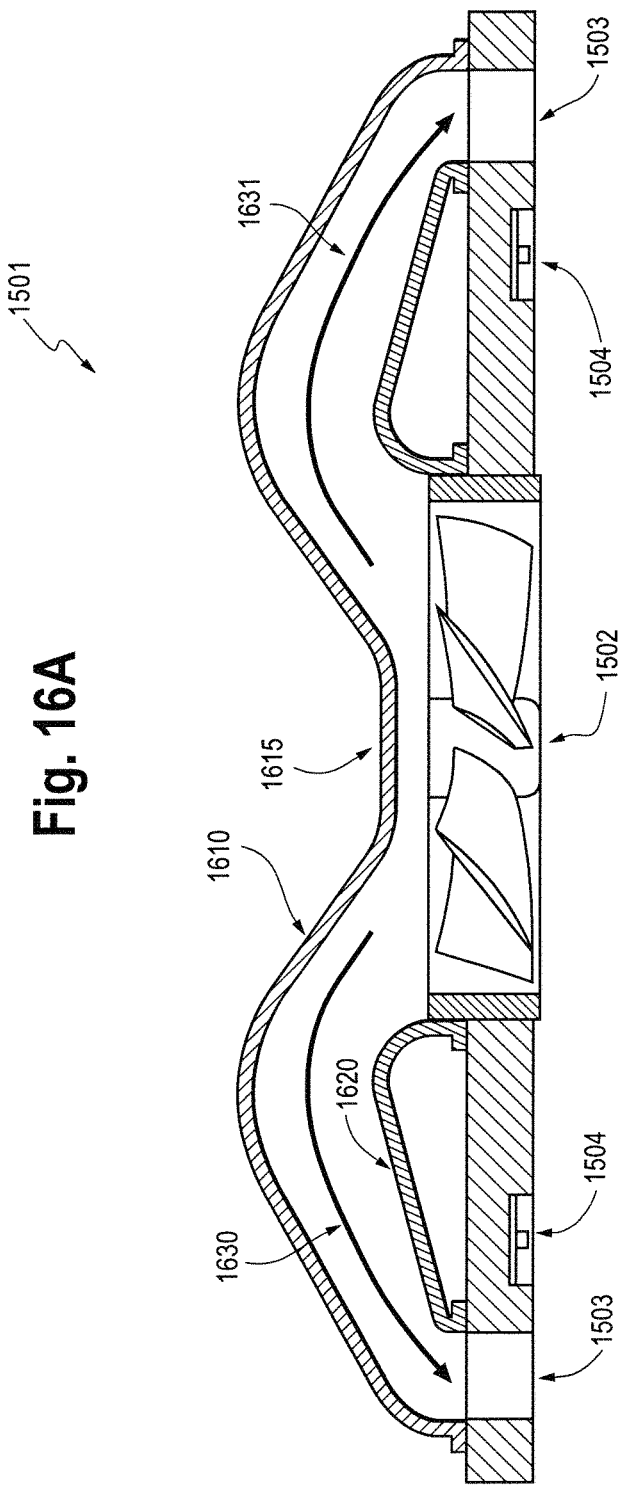
FIG. 16A is a cross section of a ceiling tile, wall tile or floor tile having a fan which directs air into a first and second airway.

As seen in FIG. 16A, which is a cut-away side view of embodiments of the inventions, an upper baffle 1610 and one or more lower baffles 1620, 1621, may act together to define one or more airway(s). For example, air may pass from a fan 1502, along airway(s) 1630, 1631 (e.g. a first airway to the left and a second airway to the right), to vents 1503. Upper baffle 1610 may comprise an apex portion 1615 which is formed in close proximity to fan(s) 1502 and/or 1503. Embodiments in which an apex portion 1615 extends into proximity with fan(s) 1502 and/or 1503 provide the advantage of improved airflow: that is because apex portion 1615 forces air to split evenly towards the left and right side. In the absence of apex portion 1615, the direction of rotation of fan(s) 1502 and/or 1503 may lead to uneven air distribution. The apex portion 1615 performs a similar function to air diversion mechanism 50 described above. Indeed, a person of skill in the art would recognize that the air diversion mechanism 50 (See e.g. FIG. 1) may be included in the embodiment of FIG. 16. Preferably, fan(s) 1502 take in air, which is released out through vents 1503. In such an arrangement, fan(s) 1502 act as an air intake and vents 1503 act as an exhaust. A person of skill in the art would recognize that it is also possible for fan(s) 1502 and/or 1503 to be configured to act as an exhaust, rather than an intake. In embodiments where LED strips 1504 are included, the flow of air through airways 1630 and 1631 may act to cool the LED strips 1504. Where two or more fans 1502 are included in an embodiment, it may be desirable, as already described above, to have them rotate in opposite directions relative to one another, e.g. one may spin clockwise while the other spins counterclockwise.

Embodiments of the invention further include the functionality of irradiating germs out of the air using UV light. Such embodiments provide the advantage of not only circulating air in an environment, but also killing viral, bacterial and fungal species which may be living in the environment's air. It is known the UV light degrades organic materials, but inorganic materials (including metals or glass) are not affected by UV light. Therefore, UV light is effective for reducing organic matter which may be airborne in the air. Reducing airborne contaminants may be important in any environment, but especially in hospitals or schools, which may be particularly susceptible to disease. Regardless of the environment, disinfecting the air of contaminants is helpful to reduce the spread of disease.

Figure 16B:
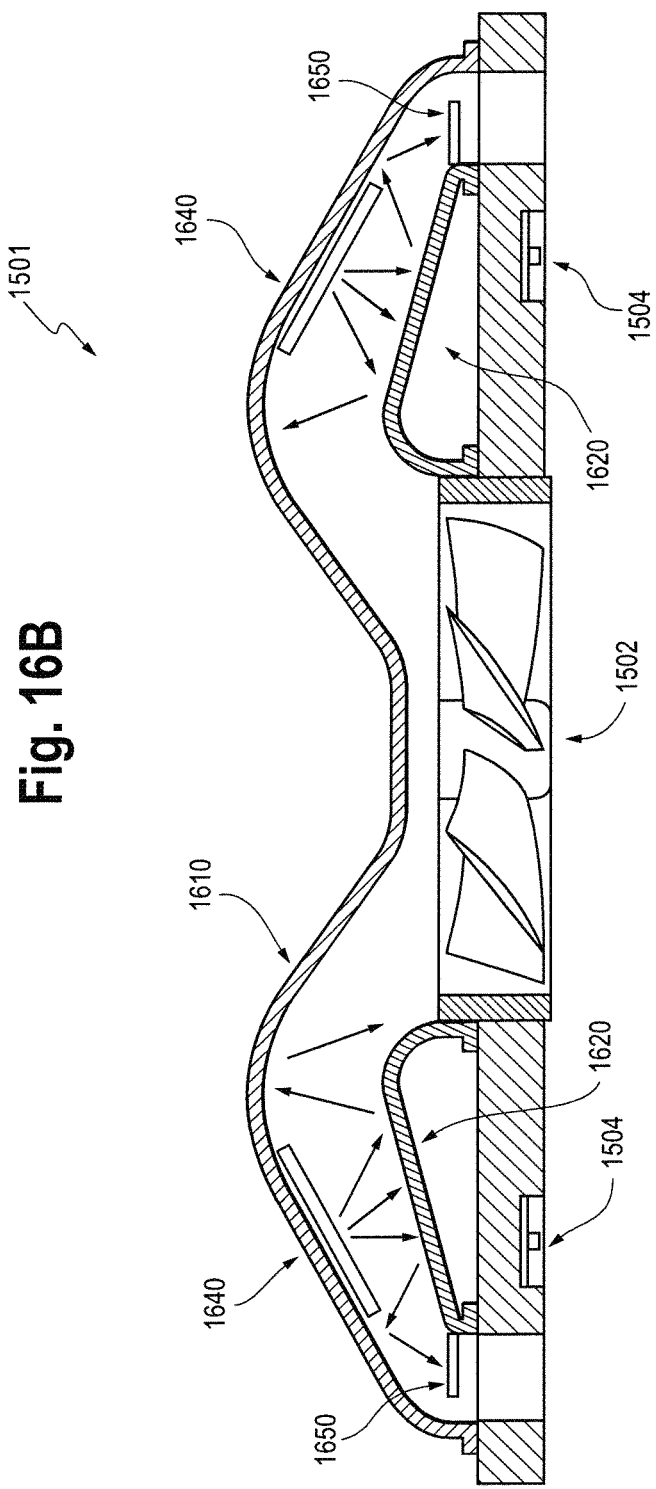
FIG. 16B is a cross section of a ceiling tile, wall tile or floor tile having a UV light source for irradiating air flow through an airway.

It is preferable to reduce or eliminate contact with UV lighting because UV light can be harmful to humans and/or animals (particularly over prolonged durations). Embodiments of the invention therefore provide the advantage of positioning a UV light source in the ceiling tile, where the UV rays may be contained in the ceiling tiles. For example, FIG. 16B illustrates exemplary UV light source(s) 1640 which are mounted inside the upper baffle 1610 and thus irradiate organic matter residing in air as air flows from the fan to the vent. A person of skill in the art would recognize that UV light sources include a power source and may optionally include an on/off controller (not shown). The UV light source 1640 may be activated by an on/off button, or it may be controlled by the remote control feature described further herein. In such an embodiment, a remote control may include the ability to activate or de-activate a UV light source 1640.

In some embodiments, light source(s) 1640 may emit UV-C light, which has a wavelength of approximately 200 to 280 nanometers. A person of skill in the art would recognize the UV-C light is optimal for irradiating airborne contaminants (such as viruses, superbugs, mold, and the like) in most environments. In embodiments of the invention, the upper baffle 1610 and/or the lower baffle 1620/1621 may be made of, or coated with, a UV-reflective material. A person of skill in the art would recognize that a UV-reflective material could include a metal, such as stainless steel, or a specialty coating. Lining the airway with a reflective material and/or reflective coating provides the advantage of creating a "kill chamber," or "kill zone" inside the airways 1630, 1631, where UV rays may bounce to increase their exposure to air passing through the airways 1630, 1631, and by extension, increase the irradiation of organic matter contained in the air.

Furthermore, some embodiments of the inventions may include a UV-screen in the form of flange 1650 which is attached to the end of airways 1630 and/or 1631 to shield UV rays from exiting the airways and entering an environment (such as a room or commercial space). In this way, including UV-screen(s) 1650 at the end of an airway Although FIG. 16B illustrates a UV source 1640 in an embodiment which is built into a ceiling tile, it should be understood that the disclosed UV source and "kill chamber" may be implemented in any of the embodiments disclosed herein.

Figure 17:
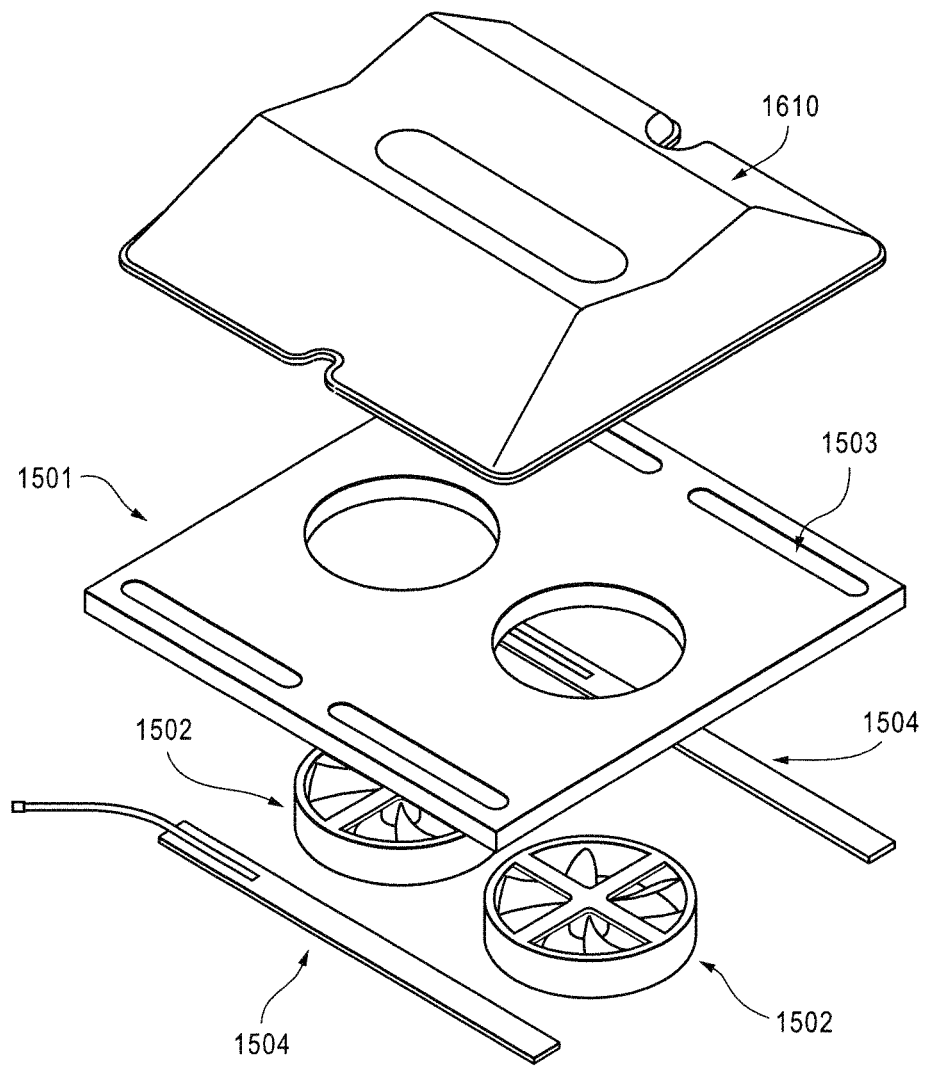
FIG. 17 is an exploded view of components of a ceiling tile, wall tile or floor tile having two fans, two LED lighting strips and an upper baffle for defining airways.

FIG. 17 shows an exploded view of components of the invention. For example, the embodiment of FIG. 17 shows a UV-C unit 1501 in which there are cut-outs for fans 1502 and vents 1503. Upper baffle 1610 is shown, sized to fit onto UV-C unit 1501. Furthermore, FIG. 17 shows exemplary LED strips 1504 (including power cord) which may be mounted on the underside of the UV-C unit 1501.

Various aspects of this disclosure may include components which are implemented directly into a structure such as a ceiling tile, wall panel or other structure such as a floor panel. As seen for example in FIGS. 18 and 19. It is contemplated that an exemplary panel 1801 may be sized as 1'×4'; 2'×2' or 2'×4' if used in a ceiling tile, although a person skilled in the art would understand that any appropriately sized tile may be used in accordance with the present inventions. Moreover, panel 1801 could be made from acoustical material, fiber, wood, metal, translucent plexiglass, styrofoam, plastic, sheet rock or drywall structures as are known to be used in industrial, commercial or residential environments. Alternatively, the panel 1801 may take the form of a light or other ornamental feature such as a statue or the like. It is further contemplated that the panel 1801 could be mounted on either a universal mounting mechanism or it could be mounted on a mobile support as shown in FIGS. 22 and 23.

Figure 18:
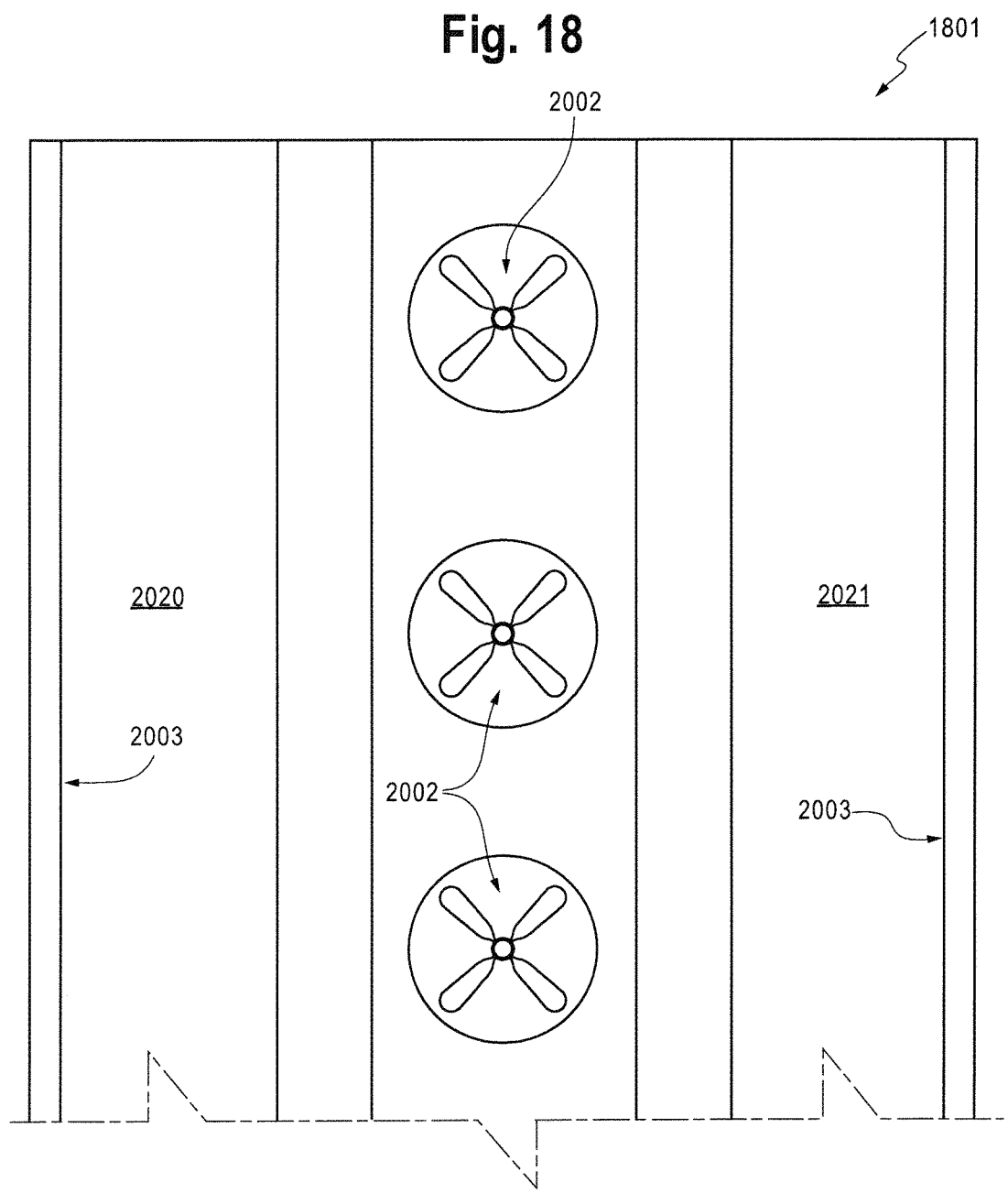
FIG. 18 is a bottom view of a tile, wall tile or floor tile having intake fans and exhaust vents utilizing a UV light source for irradiating air flowing through the chambers.
Figure 19:
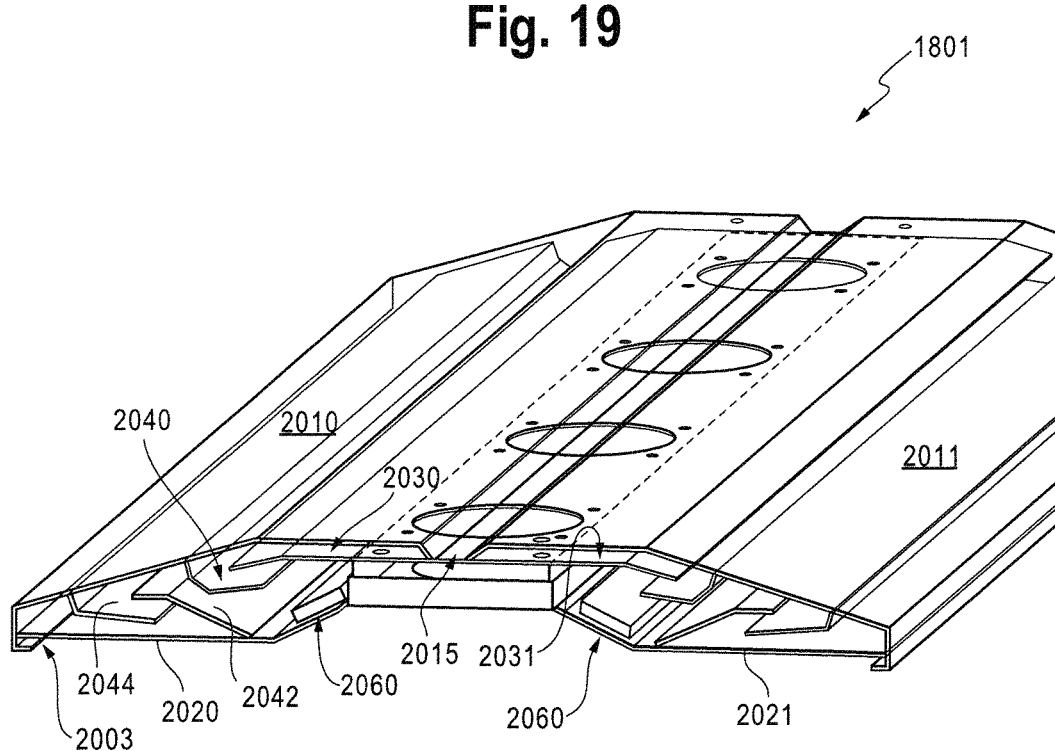
FIG. 19 is a perspective view of a tile, wall tile or floor tile having intake fans and exhaust vents utilizing a UV light source for irradiating air flowing through the chambers.

In embodiments of the inventions, panel 1801 may have one or more fans 1802 and vents 1803 cut into the panel 1801, or positioned in the ceiling grid, sometimes referred to herein as a ceiling panel. Panel cuts may be made or manufactured using waterjet cutting, die cutting, laser cutting, CNC routing, CNC knife cutting, reciprocated knife cutting or any other known techniques for cutting through tiles. Vents 1803 may take the form of elongated slot(s) extending along the edge of panel 1801, although other shapes are also contemplated. For example, FIG. 18 shows the vents 1803 as an elongated slot that runs along the entire length of the panel 1801. A person of skill in the art would understand that additional arrangements are contemplated. Optional LED strips (not shown) may be included, and may extend between the one or more fans 1802 and vents 1803.

Figure 20A:
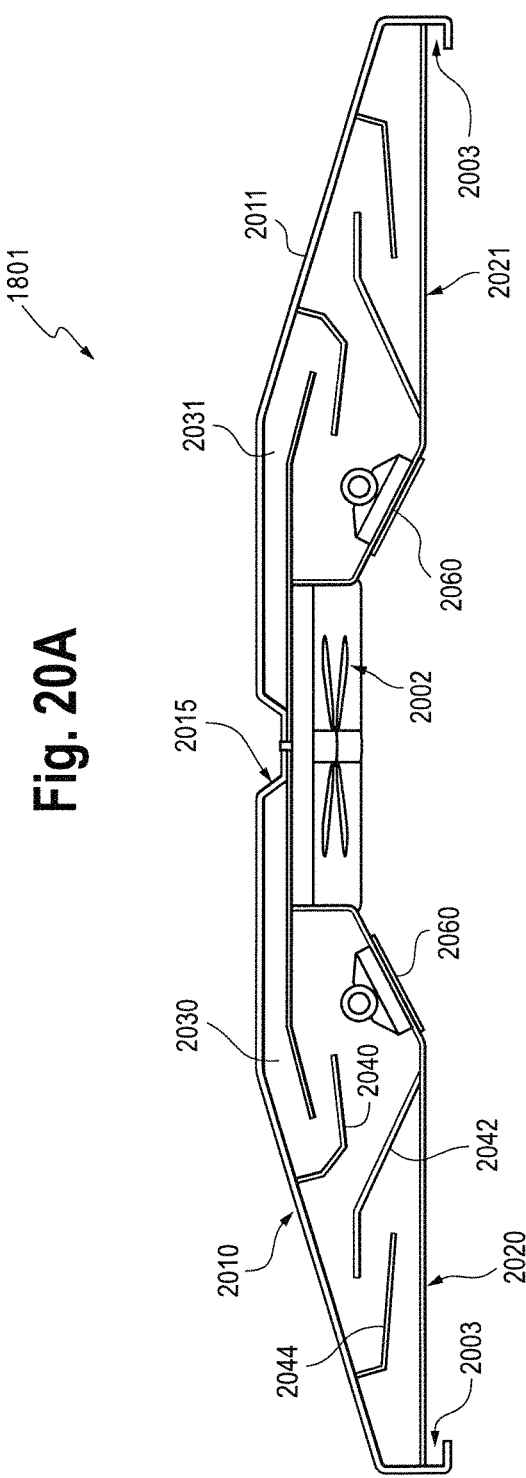
FIG. 20A is a cross section of a tile, wall tile or floor tile having a UV light source for irradiating air flow through a chamber, a raw intake, exhaust vents and various baffles.

As seen in FIG. 20A, which is a cut-away side view of embodiments of the inventions, upper baffles 2010, 2011 and one or more lower baffles 2020, 2021, may act together to define one or more airway(s). For example, air may pass from a fan 2002, along airway(s) 2030, 2031 (e.g. a first airway to the left and a second airway to the right), to vents 2003. Upper baffles 2010, 2011 may form air deflection mechanism 2015 which is formed in close proximity to fan 2002. Alternatively, the deflection mechanism 2015 may consist of a separate structure. Embodiments in which an air diversion mechanism 2015 extends into proximity with fan 2002 provides the advantage of improved airflow: that is because the air diversion mechanism 2015 forces air to split evenly towards the air chambers 2030 and 2031. In the absence of air diversion mechanism 2015, the direction of rotation of fan 2002 may lead to uneven air distribution. The air diversion mechanism 2015 performs a similar function to air diversion mechanism 50 described above. Indeed, a person of skill in the art would recognize that the air diversion mechanism 50 (See e.g. FIG. 1) may be included in the embodiment of FIGS. 20A and 20B. Also included within the air flow airways 2030 and 2031 are a series of baffles 2040, 2042 and 2044. The baffles operate to direct the air flowing through the airways 2030 and directs the air through an outlet vent 2003. The baffles 2040, 2042 and 2044 form what is called the kill zone. There may be included in the embodiment shown in FIG. 20A are UV light systems 2060. The UV lights 2060 operate to irradiate fungi, bacteria and viruses form the air circulating through the system 2001. The UV lights operate within a wavelength of approximately 200 to 280 nanometers. The bulbs used in the UV light are typically referred to the UV-C light spectrum. The UV-C bulbs operate along the specific wavelength of ultra-violet lights or light diffusing optical fibers. The UV-C light sources are typically referred to as T-5, T-8 or similarly type of LED lighting fixtures. The embodiment in FIGS. 20A and 20B may include an indicator light (not shown) to indicate when the UV-C light source is operating within the chambers 2030 and 2031. While the UV-C light source is shown in FIGS. 20A and 20B, the LED light 20 depicted in FIGS. 1-7, 13 and 14 above could be replaced with the UV-C light source.

The UV-C lights 2060, emitting light along a wavelength of 200 to 280 nanometers, have been deemed to have potentially harmful effects on humans. The baffles 2040, 2042 and 2044 operate to maintain the light emitted by the UV-C light fixture 2060 within the fixture so that little, if any, UV-C light is emitted from the fixture through the fans 2002 or the vent 2003. The baffles 2040, 2042 and 2044 may be positioned on the opposite side of the airway 2031. Preferably, fan(s) 2002 take in air, which is released out through vents 2003. In such an arrangement, fan(s) 2002 act as an air intake and vents 2003 act as an exhaust. A person of skill in the art would recognize that it is also possible for fan(s) 2002 and/or 2003 to be configured to act as an exhaust, rather than an intake. In embodiments where UV-C lighting is included, the flow of air through airways 2030 and 2031 may act to irradiate the air to eliminate germs, viruses, bacteria, fungi or the like. Where two or more fans 2002 are included in an embodiment, it may be desirable, as already described above, to have them rotate in opposite directions relative to one another, e.g. one may spin clockwise while the other spins counterclockwise.

Figure 20B:
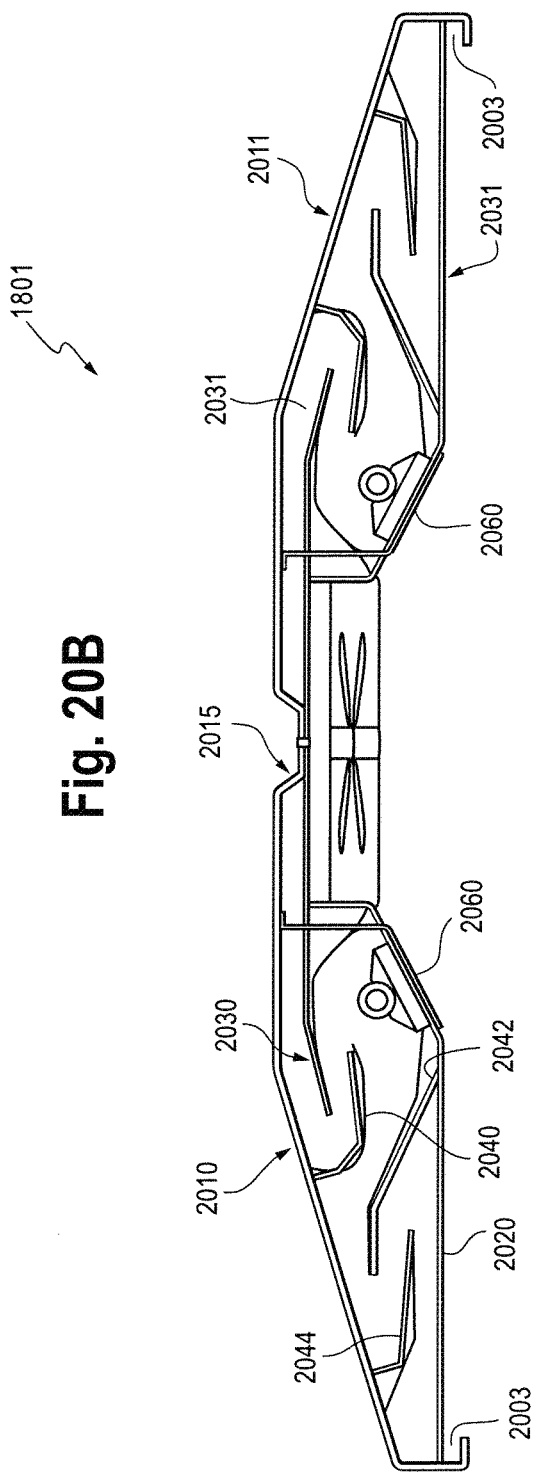
FIG. 20B is a cross section of a tile, wall tile or floor tile having a UV light source for irradiating air flow through a chamber, a raw intake, exhaust vents and baffles with a reflective material.

In the embodiment shown in FIG. 20B, the light source(s) 2060 may emit UV-C light, which has a wavelength of approximately 200 to 280 nanometers. A person of skill in the art would recognize that the UV-C light is optimal for irradiating airborne contaminants (such as viruses, superbugs, mold, bacteria, fungus and the like) in most environments. In embodiments of the invention, the upper baffle 2010 and/or the lower baffle 2020 and 2021 may be made of, or coated with, a UV-reflective material. A person of skill in the art would recognize that a UV-reflective material could include a metal, such as stainless steel, or a specialty coating. Lining the airway with a reflective material and/or reflective coating provides the advantage of creating a "kill chamber," or "kill zone" inside the airways 2030 and 2031, where UV rays may be deflected within the "kill chamber" to increase their exposure to air passing through the airways 2030 and 2031, and by extension, increase the irradiation of organic matter contained in the air. Furthermore, in the embodiment of FIGS. 20A and 20B, the baffles 2040, 2042 and 2044 located in airways 1630 and/or 1631 operate to (1) shield UV rays from exiting the airways and entering an environment (such as a room or commercial space) and (2) to increase the intensity the air is exposed to the UV-C light emitted by the UV-C light source 2060, and (3) increase the duration of air flowing through the airway 2030 and 2031 is exposed to the UV-C light. The baffles 2040, 2042 and 2044 operate to extend the time that the air flows along the kill zone thus increasing the number of germs that are killed within the fixture. An actual test of a unit utilizing the UV-C light source 1640 was conducted. The study was conducted to verify the unit's microbial reduction efficacy of aerosolized contaminants. The unit was mounted on the ceiling in a sealed 11' 10"×11' 10"×8'1" (1125 cu. ft.) controlled environment room. The unit's fan and UV lamps were powered on and allowed to warm up over the course of 2-hours as part of conditioning. Aliquots of the microorganisms were added to a pre-sterilized nebulizer reservoir. The testing room was sealed; all equipment activation was performed remotely. The nebulizer was powered to aerosolize the microbial suspension. Following 5 minutes, the UV-C light source and fans were powered on. Samples of the air were collected immediately after unit activation using Bio-aerosol air impinger (Biosampler, SKC, Inc.). The air sample were collected over the course of three minutes. Air samples were collected again following 1 and 2-hours following start. The system was deactivated, and the room was exhausted for 25 minutes before entry for sample retrieval and subsequent analysis. The study was repeated as described with only the fans running and then again with the unit completely powered off. All collected samples were analyzed in triplicate at the minimum as per standard lab operating procedures. Analysis was conducted as per laboratory's accredited ISO17025:2005 methodology: bacteria were analyzed as per SM 9215 (APHA 2012) and MS-2 as per EPA 1602. Analysis was conducted using calibrated and/or validated Instruments to traceable standards (NIST). All QC was within method acceptance limit. No general environmental conditions are specified in the standard or have been identified that could affect the test results or measurements.

The test results demonstrated the following:

The test resulted in a finding that 99.6% of *K. pneumoniae* was eliminated from the air after 1-hour of operation, and 99.998% of *K. pneumoniae* was eliminated from the air after 2-hours of operation. There was a 30% reduction of *K. pneumoniae* from the air after 1-hour of operation when the UV light source was not activated. The tests further found that 98.4% of the MSZ virus was eliminated from the air after 1-hour of operation and 99.6% of the MSZ virus was eliminated after 2-hours of operation. There was a 27.2% reduction of MSZ virus from the air after 1-hour of operation when the UV light source was not activated.

Figure 21:
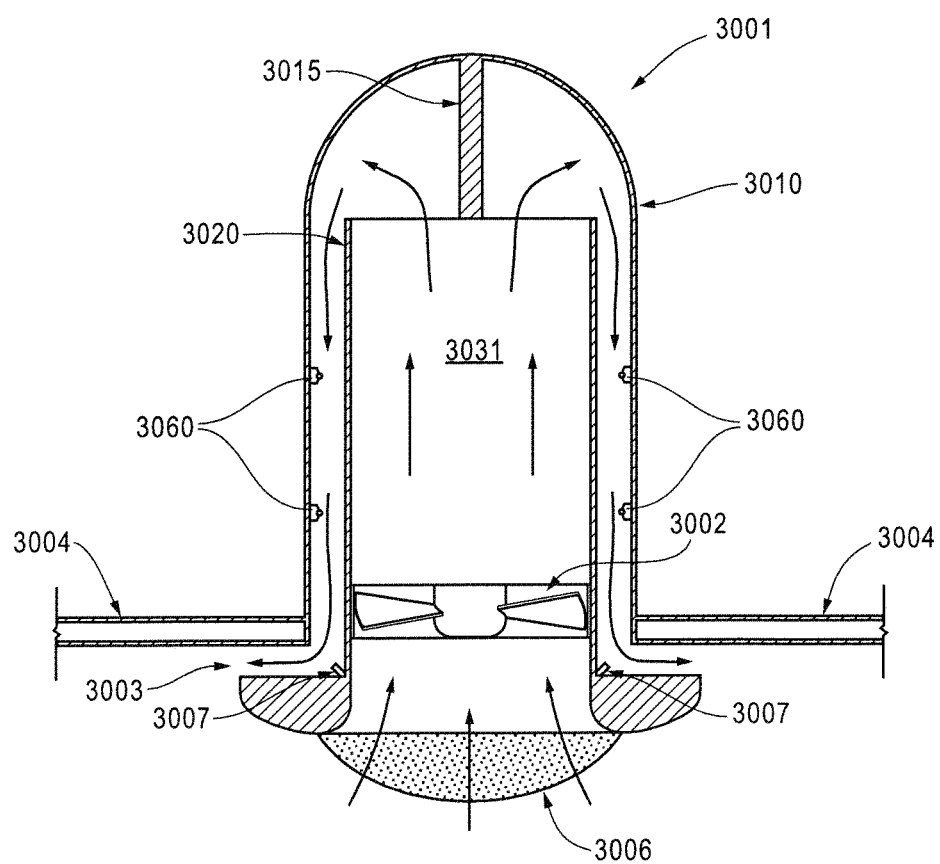
FIG. 21 is a cross sectional view of an optional light source incorporating the present invention in a canned ceiling light.

There is yet another configuration for the present invention embodied in a can or recessed light fixture as shown in FIGS. 21 and 22. As depicted in FIG. 21, the recessed UV-C fixture 3001 is in the form of a recessed or can lighting that is adapted to accommodate a light and fit relatively flush to a ceiling. The UV-C fixture 3001 may either be surface mounted or flush mounted to a ceiling 3004. The shape of the UV-C fixture 3001 may be round, square, rectangular, oval or any shape desired by a designer. The UV-C fixture 3001 may incorporate some or all of the features depicted in preceeding FIGS. 1-20. FIG. 21 shows a cut-away side-view of the embodiment having an upper baffle 3010 and a lower baffle 3020. The upper baffle 3020 may be a nominal sealed fixture with an outside diameter of 4, 6, 8 or 10 inches with a nominal height between 6 to 12 inches. There is an inner baffle 3012 that defines a interior tunnel or kill chamber 3030 between the inner baffle 3012 and the outer baffle 3010. The diameter or size of the inner baffle is generally between one to two inches less than the diameter or size of the outer baffle 3010. Thus, the kill chamber or tunnel 3030 is generally between one to two inches wide.

The recessed UVC fixture 3001 includes a fan 3002 housed in a fan chamber. The fan 3002 operates to move air along a first airway 3031. The air is moved along an air deflection mechanism 3015 which may be in close proximity of the fan 3002 or it may be positioned in proximity to the air chamber 3031 as disclosed in the embodiment of FIG. 21. The deflection mechanism 3015 may be incorporated into the outer baffle 3010 or the deflection mechanism 3015 may be constructed of a separate structure. The fan 3002 may be an inverted fan pulling air from below the ceiling 3004 through a decorative exterior screen 3006 into the fan chamber housing the fan 3002. The invented fan 3002 of the preferred embodiment acts to impart a constant pressure into the fan chamber to move air from below the ceiling 3004 through the decorative screen 3006 and fan 3002 into the air chamber 3031. The air is eventually pushed into the kill chamber 3030 and through the vent 3003 back into a position below the ceiling 3004. There is a seal 3007 between the outside baffle 3010 and the ceiling 3004 to ensure that the air leaving the kill chamber 3030 through the vent 3003 does not escape from the air purification fixture 3001. There is a light protection plate 3007 which operates to direct the UV-C light into the kill chamber and prohibit the UV light emitted from the UV-C light system 3060 from exiting the kill chamber 3030.

The kill chamber 3030 includes a UV-C light system 3060 which may include one or more UV light sources. The UV-C light system 3060 operate to irradiate fungi, bacteria and viruses form the air circulating through the system 3001. The UV-C light source 3060 operates within a wavelength of approximately 200 to 280 nanometers. The bulbs used in the UV-C light source 3060 are typically referred to operate within the UV-C light spectrum. The UV-C bulbs operate along the specific wave length of ultra-violet lights or light diffusing optical fibers. The UV-C light sources 3060 are typically referred to as T-5, T-8 or similarly type of LED lighting fixtures. The embodiment in FIG. 21 may include an indicator light (not shown) to indicate when the UV-C light source 3060 is operating within the chambers 3030.

The UV-C lights 3060, emitting light along a wavelength of 200 to 280 nanometers, have been deemed to have potentially harmful effects on humans. There are screens 3042 and 2044 which operate to maintain the light emitted by the UV-C light fixture 3060 within the fixture so that little, if any, UV-C light is emitted from the fixture through the fans 3002 or the vent 3003. The baffles 3007 may be positioned on the opposite side of the airway 3030. Preferably, fan(s) 3002 take in air, which is released out through vents 3003. In such an arrangement, fan(s) 3002 act as an air intake and vents 3003 act as an exhaust. A person of skill in the art would recognize that it is also possible for fan(s) 3002 and/or 3003 to be configured to act as an exhaust, rather than an intake. In embodiments where UV-C lighting is included, the flow of air through airway 3031 to airway or kill chamber 3030, where in airway 3030 may act to irradiate the air to eliminate germs, viruses, bacteria, fungi or the like. Where two or more fans 3002 are included in an embodiment, it may be desirable, as already described above, to have them rotate in opposite directions relative to one another, e.g. one may spin clockwise while the other spins counterclockwise.

In the embodiment shown in FIG. 21, the UV-C light source(s) 3060 may emit UV-C light, which has a wavelength of approximately 200 to 280 nanometers. A person of skill in the art would recognize the UV-C light is optimal for irradiating airborne contaminants (such as viruses, superbugs, mold, bacteria, fungus and the like) in most environments. In embodiments of the invention, the outer baffle 3010 and/or the inner baffle 3020 may be made of, or coated with a UV-reflective material. A person of skill in the art would recognize that a UV-reflective material could include a metal, such as stainless steel, or a specialty coating. Lining the airway with a reflective material and/or reflective coating provides the advantage of creating a "kill zone" inside the kill chamber 3030, where UV rays may be deflected within the kill chamber 3030 to increase their exposure to air passing through the airways 3030, and by extension, increase the irradiation of organic matter contained in the air. Furthermore, the screens 3007 operate to (1) shield UV rays from exiting the airways and entering an environment (such as a room or commercial space) and (2) to increase the intensity the air is exposed to the UV-C light emitted by the UV-C light source 3060, and (3) increase the duration of air flowing through the airway 3030 is exposed to the UV-C light. The baffles 3042 and 3044 operate to extend the time that the air flows along the kill zone thus increasing the number of germs that are killed within the fixture. The UV-C fixture 3001 may also include a light fixture (not shown) that may be incorporated around the air intake 3006.

FIG. 22 shows the UV-C unit 1501 (in FIGS. 15, 16A and 16B) or the panel 1801 (in FIGS. 18, 20A and 20B) attached to a universal mounting mechanism 2201. While the preferred embodiment of the UV-C unit 1501 and the panel 1801 are described herein, it should be understood that the unit depicted in FIGS. 1-7 and 13-14 could utilize a UV-C light source and be attached to the universal mounting mechanism 2201 as well. The UV-C unit 1501 (or panel 1801) is of the type discussed above in FIGS. 15, 16A, 16B, 18, 20A and 20B. The UV-C unit 1501 (or panel 1801) is configured to be a self-contained unit, such that the fan 1502, baffles 1620 and UV-C light source 1640 are all contained within an external housing 2202. The external housing includes a mount 2203. The mount 2203 may be a bracket 2203, loop (not shown), quick-connect coupling (not shown) or other type of known mounts. The type of mount is not an important feature of the invention. The mount 2203 functions to affix the UV-C unit 1501 (or panel 1801) to a frame 2204. The frame 2204 of the preferred embodiment includes three rigid supports 2205, 2206 and 2207. The rigid supports 2205, 2206 and 2207 may be made out of metal, wood, plastic or other type of rigid material. Rigid supports 2205 and 2206, as well as rigid supports 2206 and 2207, may be affixed to each other with an articulating joint. The articulating joints operate to allow the rigid supports 2205, 2206 and 2207 to be maneuvered in a manner to position the UV-C unit 1501 (or panel 1801) in a desired position relative to the base 2208. The base 2208 is affixed to the frame 2204. The base may be weighted. The base 2208 acts as a counterweight and support for the UV-C unit 1501 (or panel 1801).

The base 2208 may be replaced with a universal mounting mechanism 2209, or the universal mounting mechanism 2209 may be attached to the base 2208. It should be understood that the universal mounting mechanism 2209 could be affixed to one of the rigid supports 2205, 2206 or 2207. The universal mount may be any type of mount that would permit the universal mounting mechanism 2201 to be mounted to a wall or piece of furniture. A clamp is shown in FIG. 22 as the universal mounting mechanism 2209. The universal mounting mechanism 2209 could be a clamp, a suction mount, a vice or other similar types of mounts. For example, the universal mounting mechanism 2201 could be affixed to a desk, chair or crib. It could also be attached to a wall if desired. The UV-C unit 1501 (or panel 1801) is operated by electricity to power the UV-C light source and fan so the universal mounting mechanism 2201 should be placed within close proximity to an electrical source such as an outlet.

FIG. 23 shows the UV-C unit 1501 (in FIGS. 15, 16A and 16B) or the panel 1801 (in FIGS. 18, 20A and 20B) attached to a mobile support unit 2301. While the preferred embodiment of the UV-C unit 1501 and the panel 1801 are described herein, it should be understood that the unit depicted in FIGS. 1-7, 13 and 14 could utilize a UV-C light source and be attached to the mobile support unit 2301 as well. The UV-C unit 1501 (or panel 1801) is of the type discussed above in FIGS. 15, 16A, 16B, 18, 20A and 20B. The UV-C unit 1501 (or panel 1801) is configured to be a self-contained unit, such that the fan 1502, baffles 1620 and UV-C light source 1640 are contained within an external housing 2302. The external housing 2302 could be configured to include a mount 2203. The mount 2203 may be a bracket 2203, loop (not shown), quick-connect coupling (not shown) or other type of known mounting device to connect the UV-C unit 1501 (or panel 1801). The mount 2203 functions to affix the UV-C unit 1501 (or panel 1801) to a mobile unit frame 2304. The mobile unit frame 2304 could comprise of a single rigid support. The mobile unit frame 2304 of the preferred embodiment includes a plurality of rigid supports 2304(a) and 2304(b). The rigid supports 2304(a) and 2304(b) may be constructed of metal, wood, plastic or other type of rigid material. Rigid supports 2304(a) and 2304(b) may be connected by an articulating joint such as a hinge 2306. The articulating joint operates to allow the rigid supports 2304(a) and 2304(b) to be maneuvered in such a manner to position the UV-C unit 1501 (or panel 1801) to a desired position relative to the base 2308. The rigid support 2304 is secured to the base 2308. While the preferred embodiment depicts a first rigid support 2304(a) and a second rigid support 2304(b), it should be understood that any number of rigid supports could be used without departing from the spirit of the invention.

The present invention utilizes an adjustment mechanism 2305 that is affixed to the first rigid support 2304(a) and second rigid support 2304(b). The adjustment mechanism 2305 includes an activation lever 2306. The activation lever 2307 operates to move the adjustment mechanism 2305 through a telescoping hydraulic mechanism to move the first rigid support arm 2304(*a*) and second rigid support arm 2304(*b*) into a position in which a user desires to place the UV-C unit 1501 (or panel 1801).

The base 2308 of the mobile support unit 2301 can be a u-shaped support. The base 2308 includes a series of wheels 2309. The wheels 2309 should include a locking mechanism to prevent the rotation of the wheels 2309 such that, when the wheels 2309 are in a locked position, the mobile support structure 2301 cannot be moved. The wheels 2309 provide for mobility of the UV-C unit 1501 (or panel 1801).

The mobile support structure 2301 can be moved to several desired locations within a structure. The UV-C unit 1501 (or panel 1801) operates to eliminate germs, viruses, bacteria, fungi or the like as described above. The UV-C unit 1501 (or panel 1801), when placed on the mobile support structure 2301 can be positioned at a variety of locations within a structure. For example, the UV-C unit 1501 (or panel 1801) can be positioned in a first room for a period of time to operate to improve the air quality within the first room and then maneuvered to a second room to operate to improve the air quality in the second room.

It should be understood that the LED light and fan within the UV-C unit 1501 (panel 1801) are operated by electricity. As such, the mobile support unit 2301 should be placed within close proximity to an electrical source such as an outlet. Alternatively, the LED light and fan of the UV-C unit 1501 (panel 1801) could be powered by a battery or the like.

While specific combinations of elements are disclosed in specific embodiments, it should be understood that any combination of the different features may be utilized in the combined fan. It is understood that elements from each of the embodiments may be utilized in any or all of the other embodiments without departing from the spirit of the invention.

The foregoing disclosure and description of the invention are illustrating and explanatory thereof, and various changes in the size, shape and materials as well as in the details of illustrated construction may be changed without departing from the spirit of the invention.

It is understood that the invention is not limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An air purifier, comprising:
   a housing for installation in a ceiling of a building space wherein the housing includes a fan portion, a UV light kill chamber and an outlet portion;
   a UV light kill chamber in the housing having a first and a second opposing ends configured to direct a flow of air in a flow direction extending between the first and the second opposing ends of the UV light kill chamber;
   a UV light source positioned in the UV light kill chamber configured to emit UV light source to irradiate the air flowing through the UV light kill chamber;
   an inlet portion of the housing communicated to the fan portion for permitting flow of the air from the building space via the inlet portion, through the fan to a fan exit portion;
   an air diversion mechanism configured to direct air from the fan exit portion to the first opposing end of the UV light kill chamber and further configured to prevent light emitted from the UV light source from exiting the air purifier;
   an outlet vent portion of the housing communicated to the UV light kill chamber at the second end thereof for permitting flow of the air between the UV light kill chamber and the building space via the outlet vent;
   a fan adjacent the inlet portion of the housing configured to generate the flow of the air to draw the flow of air from the building space through the air diversion mechanism and deliver the flow of air through the UV light kill chamber and out the outlet vent; and
   a plurality of baffles positioned in the UV light kill chamber to act as a barrier preventing light emitted from the UV light source from exiting the air purifier.

2. The air purifier of claim 1, wherein the UV light source is a UV light emitting light having a wavelength between 200 and 280 nanometers.

3. The air purifier of claim 2, wherein the UV light kill chamber includes an interior surface which includes a UV reflective material.

4. The air purifier of claim 2, wherein the flow direction of the flow of air in the UV kill chamber has a direction and the inlet portion of the housing is positioned at an angle to the flow direction.

5. The air purifier of claim 4, wherein the outlet vent is positioned at an angle to the flow direction.

6. The air purifier of claim 5, further comprising an indicator light to indicate when the UV light source is operating within the UV light kill chamber.

7. The air purifier of claim 6, further comprising an actuator to control the operation of the UV light source.

8. The air purifier of claim 2, wherein a plurality of baffles positioned in the UV kill chamber are L-shaped.

9. The air purifier of claim 2, wherein a plurality of baffles positioned in the UV kill chamber include a mounting end affixed to the housing and a distal end, the plurality of baffles are configured such that the distal ends overlap.

10. The air purifier according to claim 1, wherein the plurality of baffles are arranged in a spaced apart arrangement to provide a series of flow channels including a guiding surface.

11. The air purifier according to claim 1, wherein the plurality of baffles are arranged in a stepped, nested, spaced apart arrangement.

12. The air purifier according to claim 1, wherein the housing has first and second main walls and a first and a second side walls connecting the main walls, including an opening in the first wall to allow air to flow into the UV light kill chamber;
   wherein at least one baffle of the plurality of baffles includes a first baffle wall extending towards toward the UV light kill chamber and a second baffle wall extending generally perpendicularly to the first main walls and at least at least one baffle of the plurality of baffles includes a second wall extending towards toward the UV light kill chamber and parallel to the second main wall.

13. The air purifier according to claim 1, wherein the housing has first and second main walls and a first and a second side wall connecting the main walls, including an opening in the first wall to allow air to flow into the UV light kill chamber,
   wherein the plurality of baffles are oriented such that at least one of the plurality of baffles is configured such that a portion of a baffle wall is positioned essentially parallel to the first main wall of the housing and at least a second of the plurality of baffles is configured such that a portion of a second baffle wall extends essentially perpendicular to the first main wall of the housing.

14. The air purifier according to claim 13, wherein the plurality of baffles are arranged in a stepped, nested, spaced apart arrangement with the first walls of adjacent baffles overlapping each other in a spaced apart manner and the second walls overlapping each other in a spaced apart manner.

15. The mobile air purifying system of claim 13, wherein each baffle of the plurality thereof is L-shaped with at least one wall of each of the plurality of baffles essentially positioned perpendicular to each other.

16. The air purifier according to claim 15, wherein the plurality of baffles are arranged in a stepped, nested, spaced apart arrangement with the first walls of adjacent baffles overlapping each other in a spaced apart manner and the second walls overlapping each other in a spaced apart manner.

17. The air purifier according to claim 16, wherein the plurality of baffles have a reflective surface in proximity to the UV light source.

18. The air purifier of claim 16, wherein the UV light source is a UV light source emitting light having a wavelength between 200 and 280 nanometers.

19. The air purifier of claim 18, wherein the UV light source operates to kill at least 99% of *K. pneumoniae* from the air.

20. The air purifier of claim 17, wherein UV-C light fixture emits light capable of killing bacteria, viruses and microbes.

* * * * *